(12) United States Patent
Fischer

(10) Patent No.: US 11,642,544 B2
(45) Date of Patent: May 9, 2023

(54) MAGNETIC FIELD APPLICATOR WITH RAMP-SHAPED COIL CURRENT SIGNAL CURVES

(71) Applicant: Prof. Dr. Fischer AG, Eschen (LI)

(72) Inventor: Gerhard Fischer, Heerbrugg (CH)

(73) Assignee: PROF. DR. FISCHER AG, Eschen (LI)

( * ) Notice: Subject to any disclaimer, the term of this patent is extended or adjusted under 35 U.S.C. 154(b) by 744 days.

(21) Appl. No.: 16/253,961

(22) Filed: Jan. 22, 2019

(65) Prior Publication Data
US 2019/0344091 A1 Nov. 14, 2019

(30) Foreign Application Priority Data
Jan. 23, 2018 (DE) .......................... 102018101394.9

(51) Int. Cl.
*A61N 2/02* (2006.01)
*G01R 33/06* (2006.01)

(52) U.S. Cl.
CPC ................ *A61N 2/02* (2013.01); *G01R 33/06* (2013.01)

(58) Field of Classification Search
CPC . A61N 2/00; A61N 2/02; A61N 2/004; A61N 2/006; A61N 2/008; A61N 2/002
See application file for complete search history.

(56) References Cited

U.S. PATENT DOCUMENTS

| | | | | |
|---|---|---|---|---|
| 5,224,922 A * | 7/1993 | Kurtz | ....................... | A61N 2/02 128/898 |
| 5,480,373 A * | 1/1996 | Fischer | .................... | A61N 2/02 600/14 |
| 5,984,854 A * | 11/1999 | Ishikawa | .................. | A61N 2/02 600/9 |
| 6,234,953 B1 * | 5/2001 | Thomas | ................. | A61N 2/008 600/14 |
| 9,981,128 B2 * | 5/2018 | Wingeier | ............. | A61B 5/4076 |
| 2014/0330067 A1 * | 11/2014 | Jordan | ...................... | A61N 2/02 600/13 |
| 2015/0165226 A1 * | 6/2015 | Simon | ...................... | A61N 1/40 600/13 |
| 2017/0106201 A1 * | 4/2017 | Schwarz | ............. | A61N 5/0625 |

FOREIGN PATENT DOCUMENTS

| | | |
|---|---|---|
| DE | 202016008331 | 9/2017 |
| DE | 202016008332 | 10/2017 |
| EP | 0594655 | 3/1996 |

* cited by examiner

*Primary Examiner* — Samuel G Gilbert
(74) *Attorney, Agent, or Firm* — Faegre Drinker Biddle & Reath LLP

(57) ABSTRACT

A magnetic field applicator (1, 55) that has a ramped signal curve for the coil currents (10, 37, 44, 49) that are used, comprised of low frequency base pulses (10, 37) of the coil current with ramp-shaped rising amplitudes, which are active during a defined treatment period (1), which are a component of the pulse packets (44) composed of the base pulses (10, 37), the envelopes (17, 17a, 17b) of which, described by the amplitudes of the base pulses (10, 37) are likewise ramp-shaped, wherein the envelopes (17a, 17b, 17c) of which form the amplitudes of the base pulses (10, 37) of a rising curve segment (57) starting from close to zero, which rises until approximately the midpoint of a treatment period (11) and subsequently forms a constant curve segment (58) corresponding to a maximum current strength, until the end of the treatment period (11) (FIGS. 13-15).

14 Claims, 21 Drawing Sheets

Figure 8:
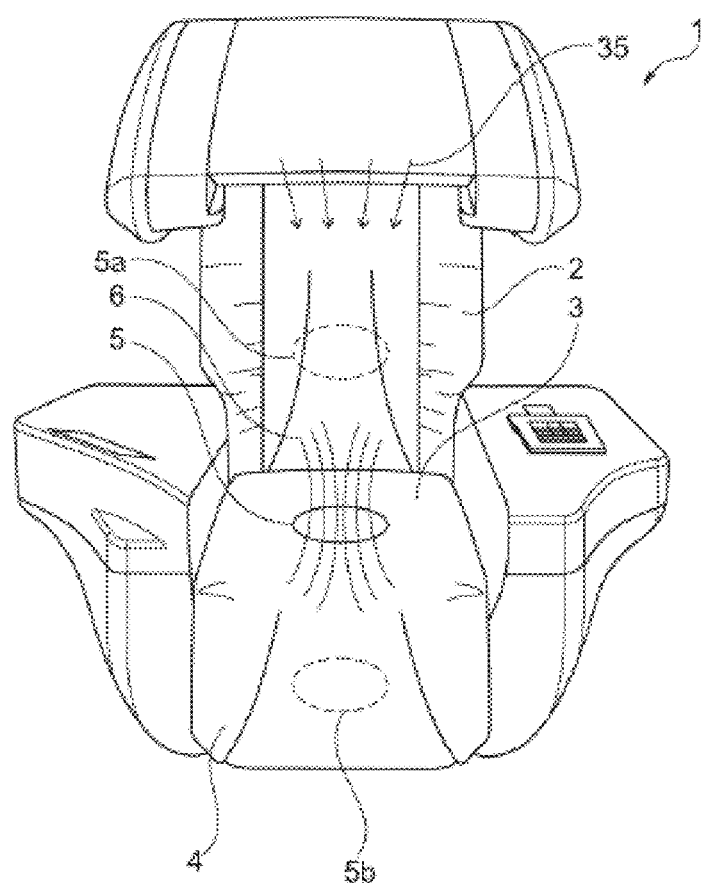

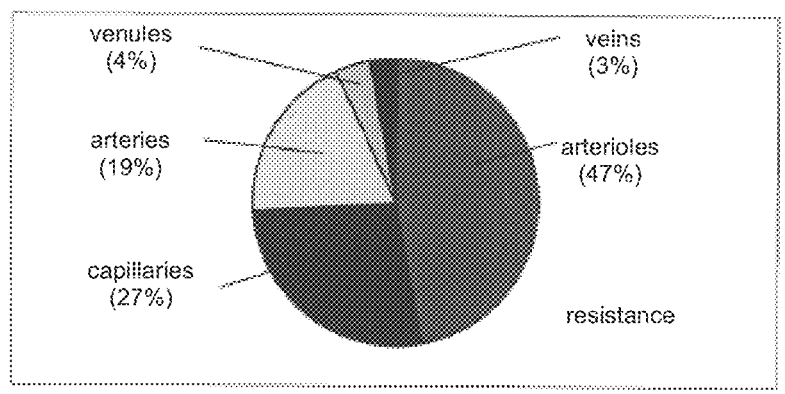
Figure 1: Relationship of the storage capacities (blood volume) C of the venous and arterial systems
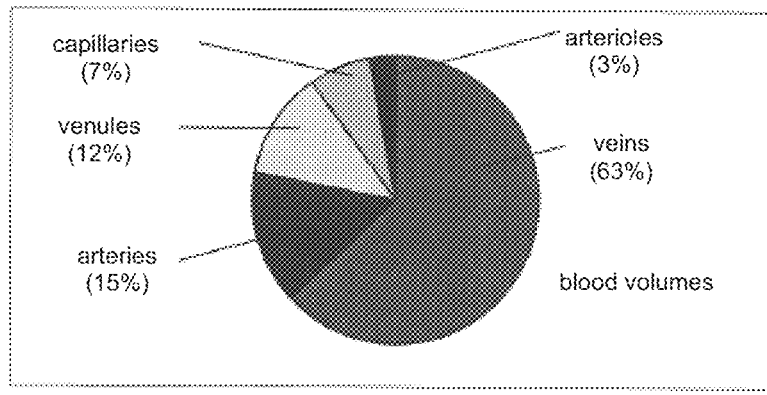
Figure 2: Distribution of blood volumes and blood flow resistance in the body's blood vessel system Figure 3: Resting blood pressure values as a function of the age of the patient and that standard range derived therefrom for the ratio RPW1
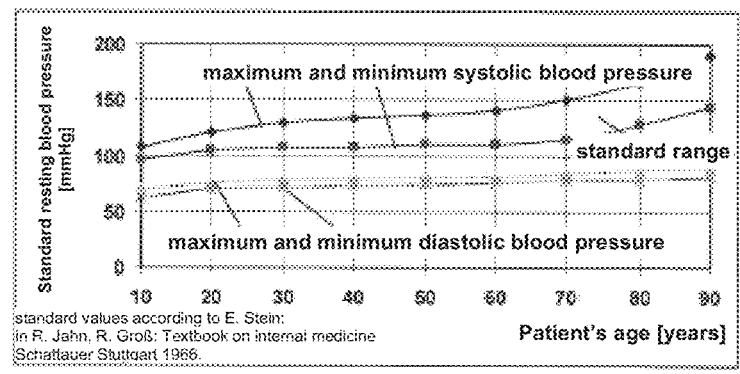
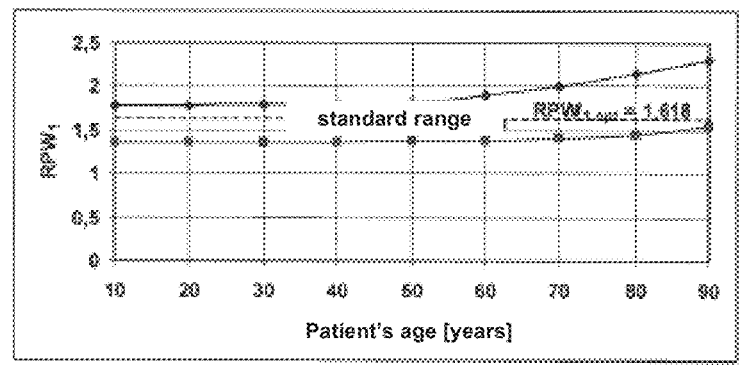

Figure 4: Blood pressure profile over time.
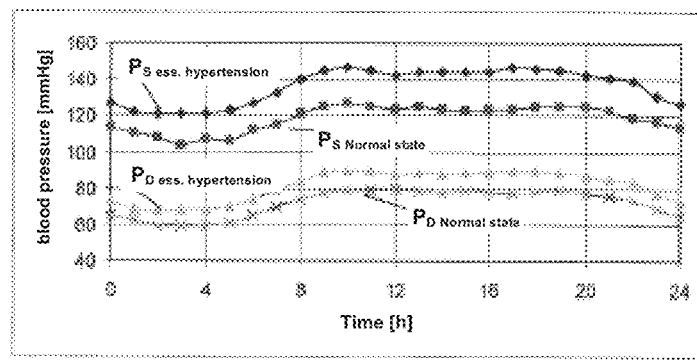
Figure 5: $RPW_1$ ratio derived from Figure 4 and hourly mean value of systolic and diastolic blood pressure.
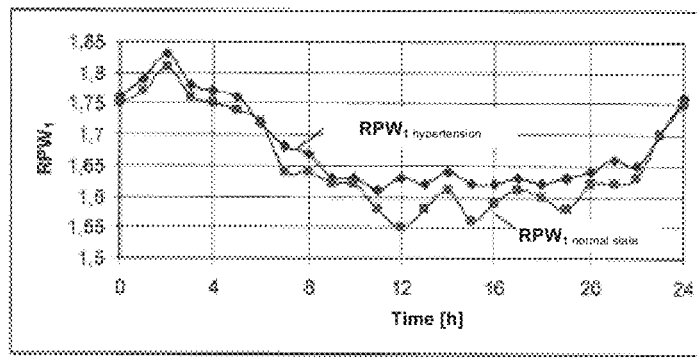

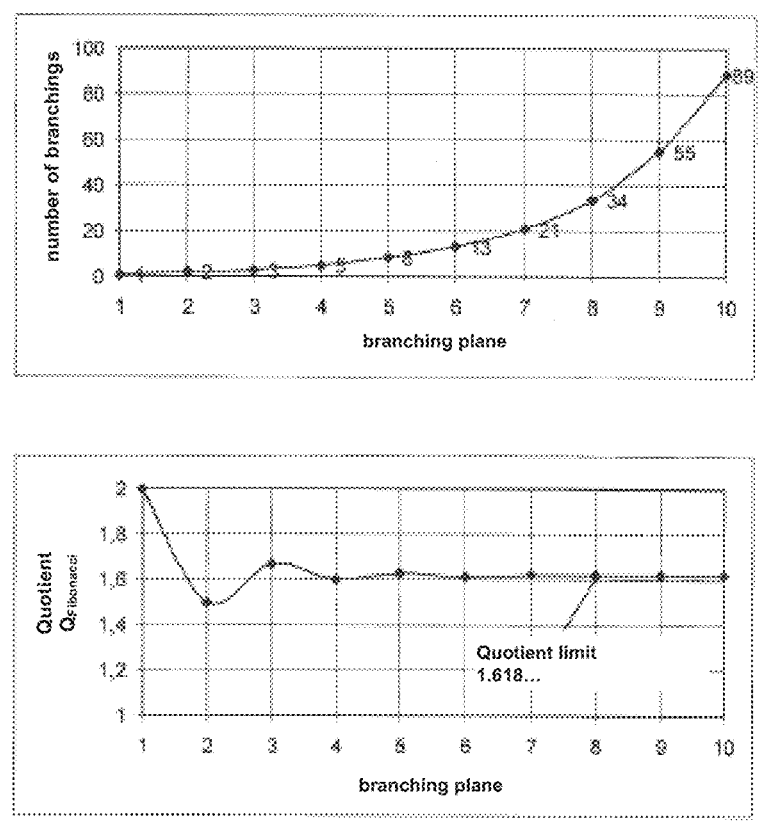
Figure 6: Number of branchings in the corresponding branching plane

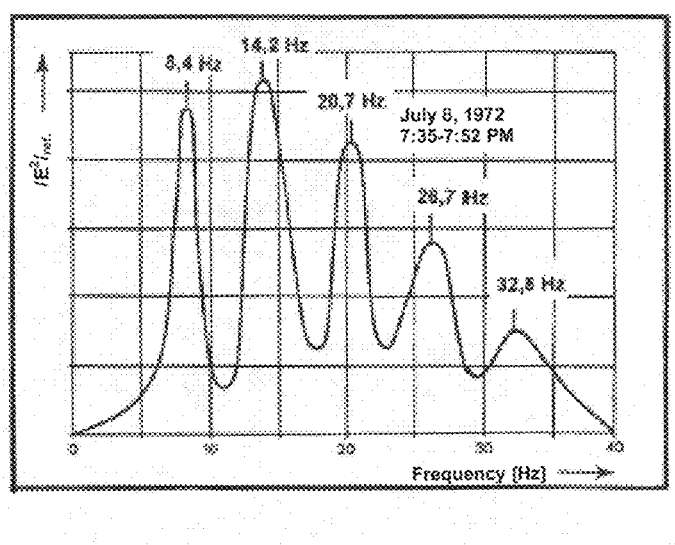
Figure 7: Spectrum of a vertical electrical field of natural signals, including the characteristic *Schumann* resonances

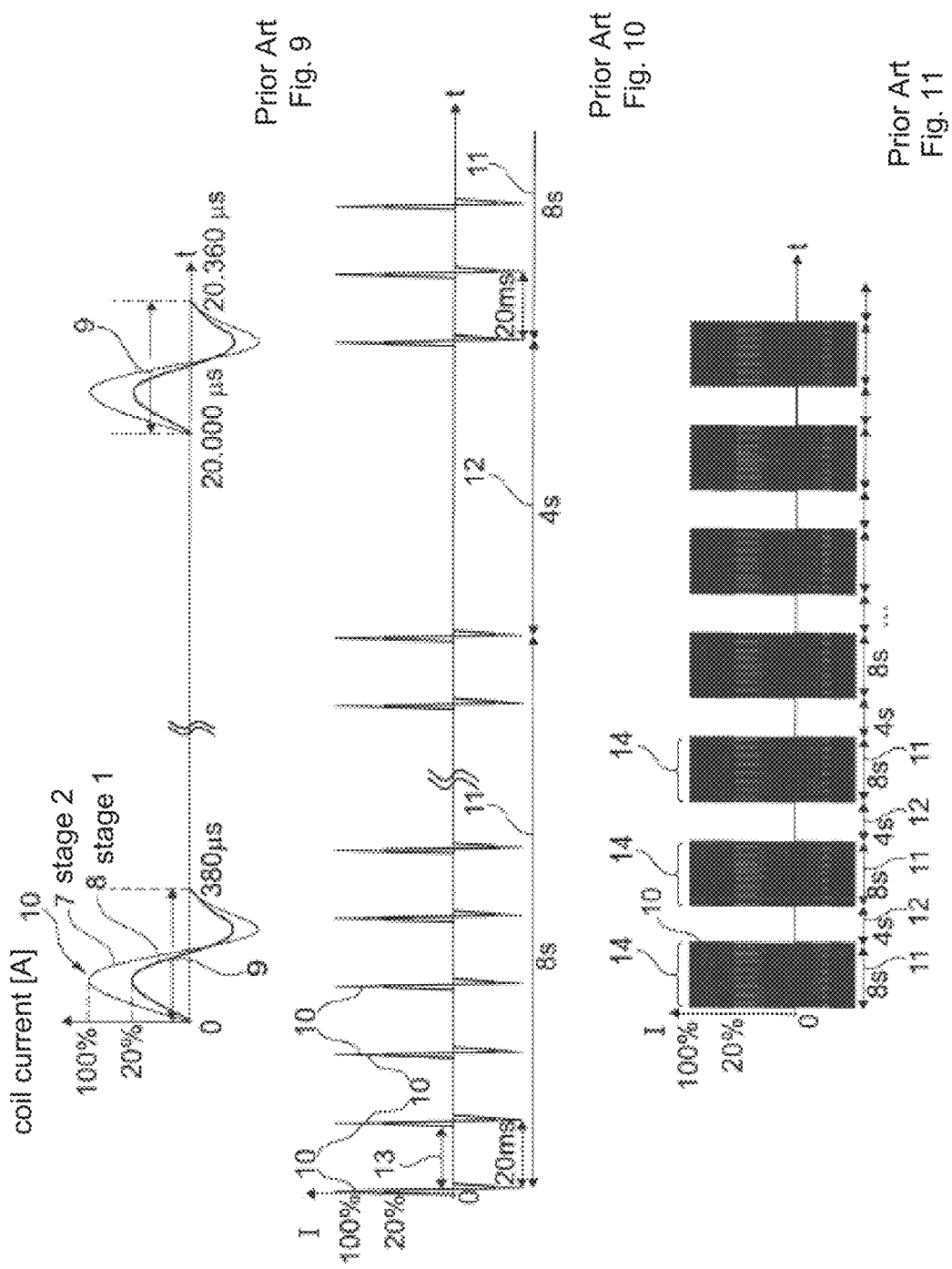

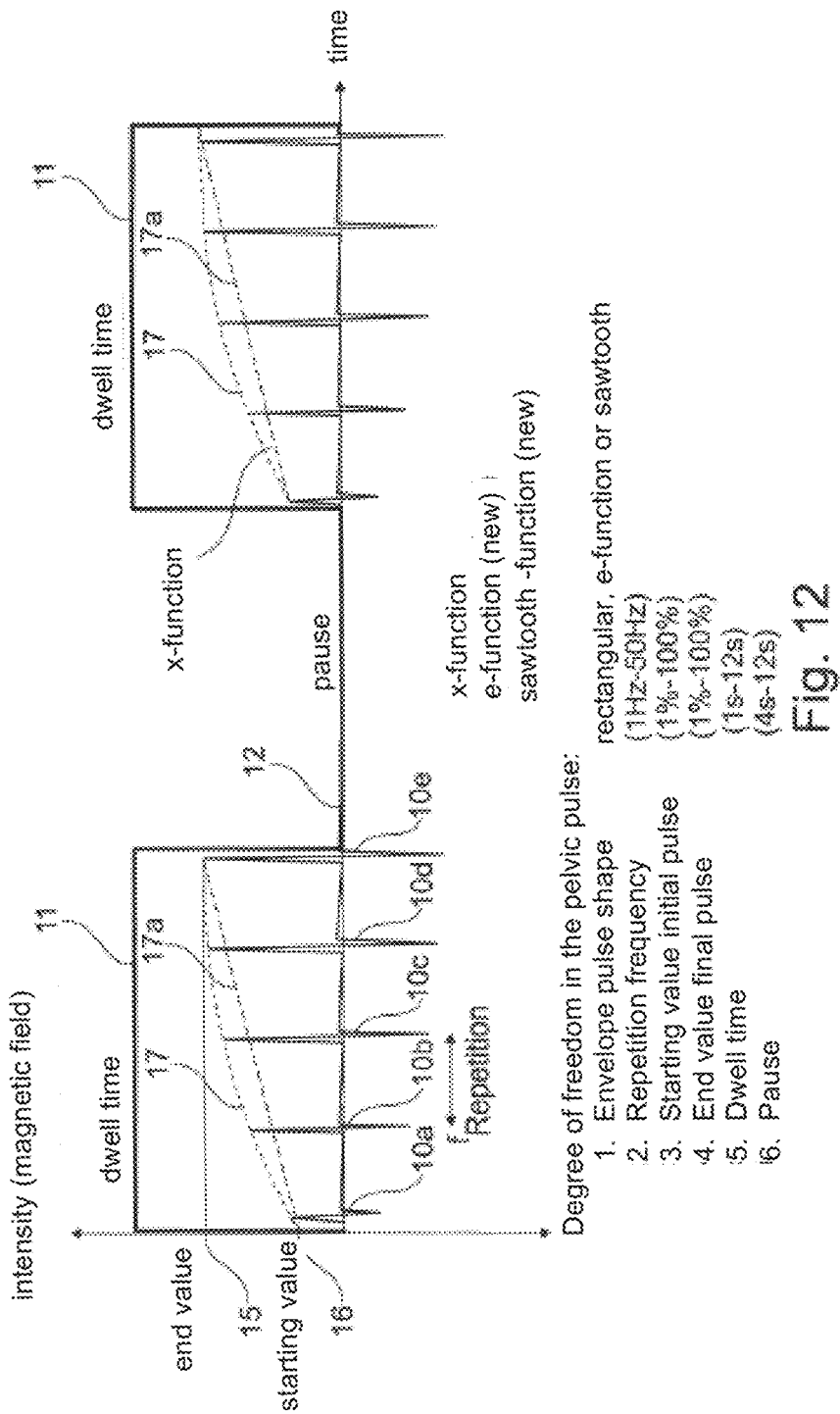

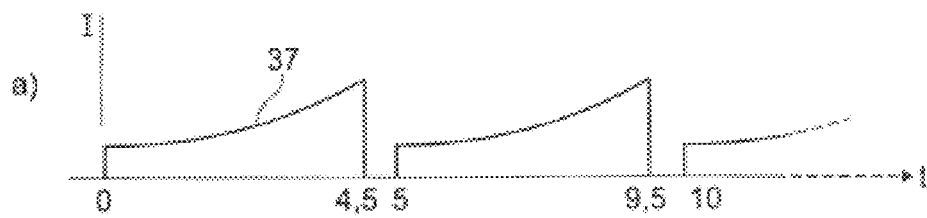
Fig. 22
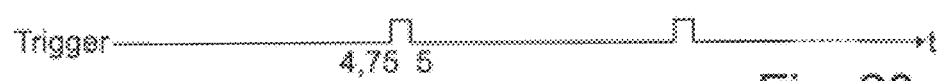
Fig. 23
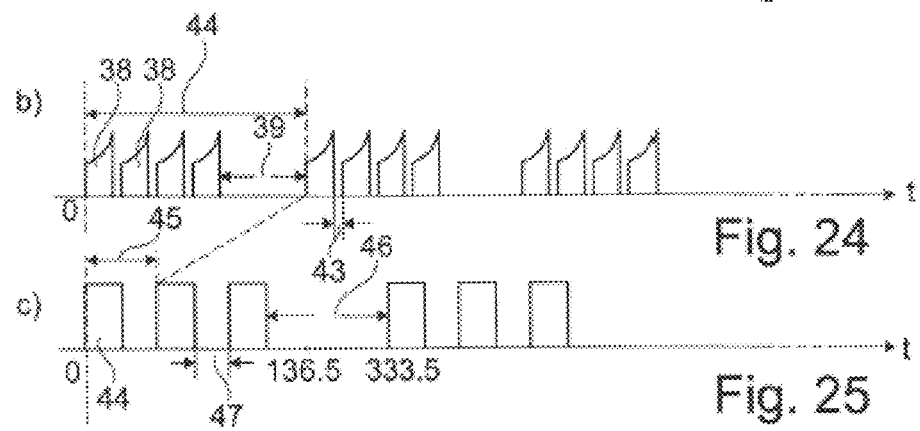
Fig. 24
Fig. 25
Fig. 26
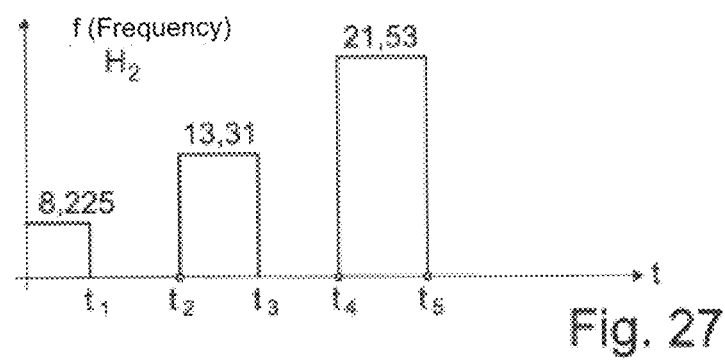
Fig. 27

MAGNETIC FIELD APPLICATOR WITH RAMP-SHAPED COIL CURRENT SIGNAL CURVES

The invention relates to a magnetic field applicator with ramp-shaped coil current signal curves.

A device of this type is known from EP 0 594 655 B1 by the same author, relating to a device functioning with low frequency, pulsed electric currents. These currents are generated by a generator, which supplies at least one magnetic field coil attached thereto with a coil current. The electromagnetic fields generated by the at least one magnetic field coil are used to treat a body region of a human or animal.

The disadvantage with EP 0 594 644 B1 is that only low field strengths of up to 30 microteslas could be generated, and the coils were not capable of generating stronger magnetic fields in the range of 1 tesla or more.

A further disadvantage was that the generated magnetic fields, induced in the manner of base pulses, were painful and felt aggressive to the person being treated, having a negative impact on the success of the treatment.

An increase in the magnetic field strength caused pain in the body region being treated, such that the treatment had to be stopped.

The use of weak magnetic fields resulted in long treatments, having a negative impact on the therapeutic effects.

The aforementioned document made use of so-called base current pulses in a range of 100 to 1000 Hz, preferably 200 Hz, the rising amplitudes of which corresponded to an exponential function. The base current pulses were superimposed with high frequency pulses with a frequency of 10 to 100 kHz. The amplitudes of the base impulse sequences formed therefrom were modulated by a periodic, curved, rising and falling modulation frequency in the range of 0.5 to 35 Hz. These pulse sequence series thus resulted in sawtooth shaped treatment current pulses.

The disadvantage in using sawtooth shaped treatment current pulses is the pain caused when the treatment current pulses increased, thus having a negative impact on the success of the therapy.

The fundamental object of the invention is therefore to further develop a device for magnetic field therapy of the type specified in the introduction, such that shorter treatment periods can be obtained with higher coil currents with the magnetic field applicator, improving the effects of the therapy.

The invention is characterized by the technical teachings of claim 1 for achieving this object.

A feature of the invention is that the envelope of the amplitudes of the base pulse form a segment rising (in a ramped manner) from close to zero, which reaches its maximum near the middle of the treatment period, and subsequently forms a constant segment lasting until the end of the treatment period corresponding to a maximum current strength.

In the prior art, the aforementioned rising, ramped curve segment first reaches its maximum current strength at the end of the treatment period. This is associated with the disadvantage that the maximum current strength is first reached at the end of the treatment period, and then abruptly stopped. As a result, the treatment was not carried out with the greatest possible current strength. Consequently, the maximum current strength of the coil current could not be exploited.

With the technical teachings of the invention, the maximum current strength is already reached by ⅓ to ⅔ of the maximum treatment period, and can then be active at this level until the end of the treatment. As a result, the maximum current strength can be used for substantially longer periods of time. Such a treatment period can last from approx. 4 to 10 seconds, followed by a pause of, e.g., 4 to 10 seconds.

In a preferred exemplary embodiment, the envelope is preferably an inclined line. It can, however, form a rising parabola, a rising exponential curve, or some other rising curve, the course of which corresponds to the amplitudes of the base pulses.

It is important that prior to starting the initial (starting) base current pulse, a relatively low current amplitude is selected, which then increases with the envelope, such that a starting ramp is formed therewith, which extends over approx. one third to two thirds of the total time of a treatment period with these base pulses, and then reaches a maximum current strength that is maintained until the end of the treatment period.

The is invention is not limited to a starting ramp that lasts over approximately one half of the treatment period in a current/time graph. It can also be shorter or longer, and it is only important that the initial base pulse and the magnetic fields generated therefrom are very slowly and gradually introduced into the tissue. As a result, voltage pulses are triggered in the tissue, which, according to the invention, slowly prepare the neurons irritated therewith for greater voltage pulses resulting from higher magnetic strengths, in order to thus prevent pain or even damage to the tissue.

It has proven to be the case that improved therapy results can be obtained with this gradual magnetic field treatment. The maximum current strengths, and the maximum magnetic field generated therewith can be maintained for a longer period of time—unlike with the prior art.

It could be proven that the therapy period (including the total of all treatment periods) could be significantly reduced, and it could also be proven that the success of the therapy could be increased with the higher current strengths used therein in comparison with the lower current strengths in known devices.

In a preferred embodiment, the envelope therefore corresponds to a rectangular or exponential function, or a sawtooth function.

The frequency of the base pulse generated during a treatment period (dwell time) lies in a range of 1 Hz to 50 Hz.

The starting value of the initial pulse of the base pulse lies in a range of 1% to 30% of the maximum amplitude. The amplitude of the base pulse generated in the rising segment corresponds to approx. 90-100% of the maximum amplitude, which is then maintained in the form of the maximum current strength in the region of the constant segment until the end of the treatment period. The treatment period (dwell time) lies in a range of 1 second to 12 seconds, and the pauses lying therebetween range from 4 seconds to 12 seconds.

Consequently, a rising ramp curve is proposed, which is formed as curve rising from a specific initial value to an end value. The end value of a base pulse preferably corresponds to a magnetic field strength of approx. 1.3 teslas, and a gradual increase in the base pulse is preferably obtained with a ramp curve starting with a magnetic field strength of 0, resulting in therapeutic effects that were so far not expected.

With the novel control of the magnetic field, a specific ramp function (envelope of the amplitudes of the base pulses) is carried out with each maximum current strength that has been set, always starting from the bottom, until the ramp function reaches the set maximum current strength, and is then continued as a constant segment of a maximum current strength, and then stopped.

Even when the same magnetic field strength used in prior art is used, it has been proven that due to the ramped envelope of the amplitudes of the base pulse, which already reach their maximum near the middle of the treatment period, muscle development in the treated muscle can be improved by 20% with a shortened treatment period.

Furthermore, the higher magnetic fields generated in this manner are particularly sharply focused, and have a significantly larger engagement area on the muscles that are treated, in particular the entire pelvic floor muscles, which was not known so far because of the use of low magnetic field strengths.

In a further development of the invention, it is provided that the treatment blocks formed by the individual base pulses now likewise follow a specific "therapy ramp" in terms of their amplitudes, meaning that the amplitudes of the treatment blocks formed by the individual base pulses follow a specific rising curve, referred to as the "therapy ramp."

This therapy ramp (rising curve) can be a straight line, a parabolic curve, or an exponential curve.

It is also preferred that the treatment blocks, for example, have a treatment period of, e.g., 8 seconds, and are composed of numerous individual base pulses, each of which induces a magnetic field pulse in the magnetic field coil.

These treatment blocks also follow a rising therapy ramp, and after eight treatment blocks, for example, that increase periodically in terms of their amplitudes, the final maximum field strengths are then obtained in the magnetic field coil.

Accordingly, a doubled ramp function is proposed, comprising a starting ramp function in the individual treatment blocks for the base current pulses generated therein, and a therapy ramp function in the sequence of numerous treatment blocks composed of individual base pulses.

In a preferred embodiment of the invention, the current control according to the invention is enabled by the gate control of a thyristor, which is connected in parallel, opposite to a free-wheeling diode.

In a further development of the present invention, a complex therapy device is used, which has a central processing unit, which assumes total control of the therapy device, and in which the size of the amplitude window, the size of the ramp function, and suchlike, can be freely programmed.

In a further development of the present invention, it is also provided that the individual base pulses and the treatment blocks formed by the individual base pulses follow a specific treatment frequency, which is preferably referred to as a Fibonacci frequency.

This shall be explained below, based on the following Fibonacci scaling with the golden ratio as the limit value and its use in diagnostics and therapies for the human cardiovascular system.

The Italian mathematician, Filius Bonacci (Fibonacci, 1170-1250) discovered this numerical series, which has resulted with its quotient/limit of two sequential numbers in the most famous scaling system in the world, the "golden ratio." Many artists, e.g. Leonardo da Vinci, have been inspired by this "golden ratio." R. N. Elliot developed a theory in the 1930s based on this, with which trends and reversals in trends could be demonstrated in nature and technology, as well as in the stock market.

The Fibonacci sequence is the infinite sequence of natural numbers, starting (originally) with the number 1 repeated, or (frequently in the modern notation) with an initial 0. Consequently, the sum of two successive numbers results in the immediately subsequent number:

0, 1, 1, 2, 3, 5, 8, 13, . . . .

(optionally) 0+1=1, 1+1=2, 1+2=3, 2+3=5, 3+5=8, 5+8=13, . . .

The numbers contained therein are called Fibonacci numbers. The sequence is named after Fibonacci, who described the growth rate of a rabbit population therewith in the year 1202. The sequence was already known, however, in ancient times, as well as by the Greeks and in India.

Further examinations have shown that the Fibonacci series also describes numerous other growth rates for plants. It appears to be a type of growth pattern in nature. This knowledge is used in the present invention.

The Fibonacci numbers have a few notable mathematical peculiarities:

Due to the relationship to the previous and subsequent numbers, growth in nature appears to follow an addition rule.

The Fibonacci sequence is directly related to the golden ratio. The further the series is continued, the closer the quotient of successive numbers is to the golden ratio (1.618033 . . . ) (e.g. 13:8=2.6250; 21:13=1.6154; 34:21=12.6190; 55:34=1.6176; etc.).

This approaching alternates, i.e. the quotients are alternately lesser and greater than the golden ratio.

Problem Addressed by the Invention

The complex system of the human circulatory system, referred to appropriately by Briggs and Peat/3/ as "an amazing example of the engineering design of nature," is known to be composed of a "supply system" (high pressure system), the "return system" (low pressure system), and the "microcirculation" (arterioles, capillaries, venules) connecting them, wherein the heart represents more than a "central pump." In order to bring the circulatory system arbitrarily close to every part of the body within an optimal period of time, with the shortest distance, and to keep the total volume of blood low, the blood supply is known to branch between 8 and 30 times before reaching each body part/3/. Although the branchings of the veins and arteries are often characterized as "chaotic" in the relevant literature, it shall be shown in this application that order exists in the human cardiovascular system that is necessarily chaotic, i.e. a determinate chaos. As a result, a Fibonacci scaling of apparently "optimal values" for the overall cardiovascular system can be derived that can form the basis for diagnostics as well as for therapy (e.g. a magnetic field therapy according to the present invention).

The work of Mandelbrot, West and Goldberger is known to have the merit that it must be assumed that the human body also exhibits a "fractal self-similarity," which repeats the same branching pattern in increasingly smaller blood vessels. "It becomes increasingly clearer that self-similarity is not just some uninteresting property, but instead is a powerful means of producing patterns" (Mandelbrot). The branching is based on Fibonacci scaling, with its limit value of 1.618034 . . . , and it must be assumed that there is a substantial scaling offset, in a manner analogous to the capillary region in lungs, for obtaining a greater efficiency, in order to achieve a "balance between physiological order and chaos."

The human cardiovascular system is regarded as being self-similar.

One fundamental of self-similarity forms the most famous scaling in the world: the number 1.618034 . . . , is obtained from the Fibonacci series $$0,1,1,2,3,5,8,13,21,34,55,\ldots \quad (1)$$

in an increasing manner as a quotient limit value, when the respective subsequent value is divided by the preceding number in the series (e.g. 55/34=1.617647). With its reciprocal of 0.618034 . . . and its square of 2.618034 . . . , the number 1.618034 . . . is also self-similar. The ratio limit 1.618034 is the known golden ratio. The value 1.618 shall be used below as an approximation thereof.

Based on the work of West and Goldberger regarding "fractal Fibonacci lung branching" Briggs and Peat have concluded that "the body is a network of numerous self-similar systems such as lungs, the vascular system, and the nervous system." It is therefore theorized that the structure of the active vascular system can be optimally modeled with sufficient approximation according to a Fibonacci scale, and the irrational number 1.618 . . . , including the relationships $$1.618^{-1} = 0.618 \quad 1.618^1 = 1.618 \quad 0.5 \times 1.618^0 = 0.5$$
$$1.618^{-2} = 0.382 \quad 1.618^2 = 2.618 \quad 0.5 \times 1.618^{-1} = 0.309$$
$$1.618^{-3} = 0.236 \quad 1.618^3 = 4.236 \quad 0.5 \times 1.618^{-2} = 0.191$$

in the sense of a (natural) constant has a dominant significance. It is thus known from "fractal lung branching" that the length relationships in the first seven generations of bronchial tubes in human lungs follow the Fibonacci scale, and the diameters of these tubes do so for even up to ten generations. There is a subsequent change in this scaling, in order obtain greater efficiency in the lungs.

The general distribution of blood volumes and blood flow resistances in the physical vascular system is shown in FIG. 1.

The following relationships can be derived from FIG. 1:

The relationship between the storage capacities (blood volume) C of the venous and arterial systems is:

$$\frac{C_{venous}}{C_{arterial}} = \frac{63\% + 12\%}{15\% + 3\%} = \frac{75\%}{18\%} = 4.17 \approx 4.236 = (1.618)^3. \quad (2)$$

The venous and arterial capacities are apparently optimized via the ratio $4.236=(1.618)^3$.

The following is obtained for the relationship of the blood flow resistance R to the blood volume C of the capillary-vein system:

$$\frac{R_{capillary,venal}}{R_{capillary,venal}} = \frac{31\%}{19\%} = 1.63 \approx 1.618. \quad (3)$$

For the capillary resistance/volume ratio, the following can be derived from FIG. 2:

$$\frac{R_{capillary}}{R_{capillary}} = \frac{27\%}{6 \ldots 7\%} = 4.154 \approx 4.236 = (1.618)^3. \quad (4)$$

With 21% by volume as the maximum O2 saturation of the arterial blood and ca. 13% by volume of O2 in venous blood, the following is obtained for the relationship thereof and thus for the optimal oxygen exploitation in the capillaries through the tissue:

$$\frac{21\% \text{ by volume } O_2}{13\% \text{ by volume } O_2} = 1.615 \approx 1.618. \quad (5)$$

The optimization of the oxygen extraction by the tissue via the number 1.618 appears to be exemplary for the self-similar structuring of the circulatory system, and even for the self-similar unit of structure and function of the "small circulatory system," as shown by the fractal Fibonacci lung branchings.

As a standard value for the cardiovascular system found in a normal subject (20 to 30 years old), the following is given:

heart rate: 70-75 min$^{-1}$ ($\equiv$1.17 . . . 1.25 Hz),
breathing rate: 16-18 min$^{-1}$ ($\equiv$0.27 . . . 0.30 Hz),
Traube-Hering waves as rhythmic changes in the arterial blood pressure: ca. 7 min$^{-1}$ ($\equiv$0.1 Hz),
blood pressure: systolic $P_S$=120 mmHg,
diastolic $P_D$=75 mmHg.

The following relationships shall be derived from these standard values:

It was already known in 1960 from Hildebrandt that there is a "coordinative relationship" between the pulse and breathing rhythms with a standard frequency ratio of 4:1, and deviations from the norm in both directions are associated with certain functional deviations in the cardiovascular system. The following relationship is derived from the given standard values:

$$\frac{\text{heart rate}}{\text{breathing rate}} = \quad (6)$$
$$\frac{1.17 \ldots 1.25 \text{ Hz}}{0.27 \ldots 0.30 \text{ Hz}} = 4.25 (\text{mean value}) \approx 4.236 = (1.618)^3.$$

It should likewise be noted that the human breathing rate also has a "coordinative relationship" to the 10 second rhythm of the blood pressure, the Traube-Hering waves. With the standard values, the following is obtained:

$$\frac{\text{breathing rate}}{\text{blood pressure periodicity}} = \quad (7)$$
$$\frac{0.27 \ldots 0.30 \text{ Hz}}{0.1 \text{ Hz}} = 2.85 (\text{mean value}) \approx 2.618 = (1.618)^2.$$

If the cardiovascular system is based on a 1.618 scaling and there are relationships based on this, it can be expected that optimally, there is also such a relationship for blood pressure values, which shall be called $V_{PS,PD}$. A deviation of this relationship from the norm could apparently likewise be attributed to functional deviations in the cardiovascular system (e.g. with peripheral arterial occlusion, or microcirculation disruptions). This relationship has been called the "relative peripheral resistance $RPW_1$" in an unpublished work:

$$V_{PS,PD} = RPW_1 = \frac{P_S}{P_D} \text{ or (with the standard values)} \quad (8)$$

$$V_{PS,PD} = \frac{120 \text{ mmHg}}{75 \text{ mmHg}} = 1.6 \approx 1.618.$$

Resting blood pressure standard values and the relationship $RPW_1$ derived therefrom as a function of the age of the patient are shown in FIG. 3. It can be seen therein that the irrational number 1.618 is the optimum, although there are deviations that occur as the age of the patient increases.

It is also known that frequency peaks for heart attacks, sudden cardiac death, and strokes occur in the early morning hours. For this reason, 24 hour blood pressure measurements are taken, both for normal as well as hypertonic subjects.

The blood pressure profiles over time are shown in FIG. 4. The relationship number $RPW_1$ determined for both groups in FIG. 4 results in the graph in FIG. 5. FIG. 5 shows the mean hourly values for systolic and diastolic blood pressure for normal subjects at n=111 and for essentially hypertonic subjects at n=109 test subjects and the relationship $RPW_1$ derived therefrom.

It is evident that:

The theory of an optimal value of the number 1.618 is confirmed.

Nearly ideal $RPW_1$ values are obtained for both normal as well as hypertonic persons between 8 AM and 8 PM.

This relationship reaches its maximum between 1 AM and 3 AM. If it increases in patients with essential hypertension, this may indicate something serious.

It shall be shown below that with the Fibonacci scaling, without prior specification of standard cardiovascular values, the (theoretically) optimum anatomical branching of the vascular system can be determined, and the functional optimums for the cardiovascular system, including the EEG frequency range, can also be determined.

Self-similar systems are comprehensively described in the relevant publications. Such a relationship is displayed by, e.g., tree structures, river courses, photographs of lightning, branchings in nerve cells (neurons), and (arterial) blood vessel branchings. If the number of branchings in the corresponding "level" of these systems is based on a Fibonacci series according to equation (1) (as a reduced series), the following is obtained:

1, 2, 3, 5, 8, 13, 21, 34, 55, . . . .

The quotient of two successive numbers in this series is represented by the graph in FIG. 6, if $$Quotient_{Fibonacci} = Q_{Fibonacci} = \frac{x_n}{x_{n-1}} \quad (9)$$

where $x_n$ and $x_{n-1}$ represent the respective last and second to last Fibonacci numbers in the series. It can be derived from FIG. 6 that after the $6^{th}$ branching level of the "tree structure," the deviations from the limit value 1.618 . . . are negligibly small. For this reason, the quotient limit 1.618 . . . , the golden ratio, is referred to as the "scaling factor" in publications.

FIG. 6 shows the number of branchings in the corresponding branching levels and the curve of the quotients $Q_{Fibonacci}$, including the limit value 1.618 . . . that is obtained if a Fibonacci series is the basis for the self-similar system (e.g. tree structure, river course, photograph of lightning, vascular branching, branching in nerve cells).

According to the relevant publications, the arithmetic mean value of the area of the cross section of the human aorta as the "trunk" of the arterial vascular branching in normal subjects is $F_{aorta} = \pi$ (cm$^2$). It is known that this irrational number, which is also necessary for calculating the area and circumference of a circle, as well as the volume of a sphere, cannot be determined precisely. There is no system for calculating it, and each subsequent decimal place is entirely random.

As a model, it shall be assumed below that the necessarily optimal bifurcation, according to the findings of West and Goldberger, follows a Fibonacci series for relatively long segments of the blood circulation, in that not only does the aorta branch according to this scaling, but the corresponding blood circulation speeds can also be determined in accordance therewith. It must therefore be possible to derive optimums for heart rates and breathing rates, as well as for other cardiovascular parameters.

If the mean area n of the cross section of the aorta according to Burton is formally scaled (divided) numerous times with the Fibonacci quotient limit value 1.618, $$F_n = \frac{\pi}{(1.618)^n} \quad (10)$$

the surprising results in Table 1 are obtained, where n is the "degree of scaling." The factors $F_1 \ldots F_n$ obtained thereby correspond to characteristic bifurcation points, which apparently reflect the "optimal" frequencies occurring in the cardiovascular system. Although the optimum frequency values for the cardiovascular system, including the EEG range, shown (in "bold") in Table 1 agree with those in the relevant publications, "intermediate frequencies" can also be seen in this table. Even if these values need to be checked more carefully, clinical experience has shown that range 0.175 . . . 0.283 . . . 0.458 Hz ($\equiv$10.5 . . . 17 . . . 27.5 min$^{-1}$) is correct for breathing frequencies in calm conditions.

The same applies for the heart rate range 0.742 . . . 1.2 . . . 1.942 Hz ($\equiv$44.5 . . . 72 . . . 116.5 min$^{-1}$). Because, however, heart rates higher than 116.5 min$^{-1}$ can occur, in particular with younger people, this is apparently only possible when the blood viscosity is normal, and not increased. On the other hand, with abnormally high heart rates, there may be a "disruption" in the vegetative components.

So-called "arterial and venal settling times" for quantifying the hemodynamic state of extremities is determined by means of "dynamic system diagnostics," and the measured standard values are compared with the values that can be derived as "optimal values" through the scaling described above. They are in relatively good agreement therewith, wherein such optimums are obtained in the scaling levels n=6, 7, 8 and 9.

Fundamental Equation for Fibonacci Scaling $F_n = \dfrac{\pi}{(1.618)^n}$

TABLE 1

The expected optimal cardiovascular parameters, including the EEG range, derived through multiple scaling of the mean aorta surface area $F_{aorta} = \pi$ [cm$^2$].

| n | Optimal Frequency $F_n$ [Hz] | Significance |
|---|---|---|
| 7 | 0.108 ($\equiv$6.5 min$^{-1}$) | blood pressure periodicity (Traube-Hering waves)/ |

TABLE 1-continued

The expected optimal cardiovascular parameters, including the EEG range, derived through multiple scaling of the mean aorta surface area $F_{aorta} = \pi$ [cm$^2$].

| n | Optimal Frequency $F_n$ [Hz] | Significance |
|---|---|---|
| 6 | 0.175 | lower limit breathing rate (?) |
| 5 | 0.283 (= 17 min$^{-1}$) | optimum breathing rate |
| 4 | 0.458 | upper limit breathing rate (?) |
| 3 | 0.742 | lower limit heart rate (bradycardia)) |
| 2 | 1.2 (= 72 min$^{-1}$) | optimal heart rate/ |
| 1 | 1.942 | natural heart rate (undamped) upper limit heart rate (tachycardia) |
| 0 | 3.142 | optimum EEG delta range |
| −1 | 5.08 | optimum EEG theta range |
| −2 | 8.225 | start of EEG alpha range, 1$^{st}$ Schumann resonance/ |
| −3 | 13.31 | end of EEG alpha range, start of EEG beta range (beta$_{1,2}$) 2$^{nd}$ Schumann resonance |
| −4 | 21.53 | EEG beta range (start of beta$_3$), 3$^{rd}$ Schumann resonance |
| −5 | 34.84 | end of EEG beta range |

The fundamental model and the scaling that is carried out deserve further examination. In particular, the reason why the factors $F_1 \ldots F_n$ derived here (the actual statistics) apparently reflect (optimal) frequencies, as is shown by the comparison with the data obtained from the relevant publications, should be analyzed. Based on the cardiac outputs passing through the aorta with is area of $F_{aorta}$ as the blood volume flow rate per second, the rules for determining the flow rate through the vascular system are used in the case of the Fibonacci scaling.

As can be seen in Table 1, when n=0 to −5, the optimal frequencies 3.142; 5.08; 8.225; 13.31; 21.53 and 34.84 Hz are obtained. It can be derived therefrom that the numbers prior to the decimal point are all Fibonacci numbers, for which reason they have been rendered in "bold." If the frequency at n=−6 is calculated, the result will be 56.37 Hz. 56 is not a Fibonacci number, however, and this frequency is therefore not regarded as relevant for the EEG range. 35 Hz is basically known to be the upper EEG frequency limit (end of he EEG beta range), as has been determined through experimental measurements.

The "optimal values" occurring in the cardiovascular system with a 1.618 scaling of n can be obtained from Table 1:

Heart rate $f_H$=1.2Hz(=72 min$^{-1}$),

Breathing rate $f_A$=0.283Hz(=17 min$^{-1}$),

Blood pressure periodicity $f_B$=0.108Hz(=6.5 min$^{-1}$).  (11)

The following relationships are thus obtained:

$$\frac{f_H}{f_A} = \frac{1.2 \text{ Hz}}{0.283 \text{ Hz}} = 4.24 = (1.618)^3, \quad (12a)$$

$$\frac{f_A}{f_B} = \frac{0.283 \text{ Hz}}{0.108 \text{ Hz}} = 2.62 = (1.618)^2. \quad (12b)$$

These optimal values, including the relationships according to equations (11) and (12), are in close alignment with the standard values and their relationships.

The EEG frequencies listed in Table 1, and their significance for the magnetic field therapy according to the invention shall be explained later.

It is clear that period doubling (or halving) in Table 1 does not occur through a scaling with 1.618, and also not directly between the number $\pi$=3.1416 . . . and the scaling constant 1.618 . . . . Only the value 1.942 is obtained here. Period doubling in the sense of the discovery by Feigenbaum in 1976 is know to have lead to the "ebullition of chaos," an increase in turbulence, and should be prevented in the cardiovascular system for stability reasons. It is also known that heart failures may occur due to congestion, if the heart rate and breathing rate become "too periodic." This indicates a severe disruption in the normal fractal relationships.

Comparison of (selected) optimal values derived in section 2 with measurements of the natural electrical and magnetic fields The space between the earth and the ionosphere for signals generated by lightning (atmospherics) represents a so-called wave guide, in which these signals are proliferated as electromagnetic waves, more or less damped according to their frequencies and the state of the ionosphere.

Most of the electrical and magnetic fields measured over the earth's surface, at least during good weather, which have a frequency of a few hertz, are the result of an excitation of the earth's ionosphere's cavity resonator by weather occurring at a great distance thereto. This phenomenon is known in physics as "Schumann resonance." It ranges from approx. 7.8 Hz to ca. 35 Hz, and is therefore identical in terms of its frequencies to the entire alpha and beta ranges in the electroencephalography (EEG). If the detections of the Schumann resonance signals are compared with those of the EEG, it is usually difficult to distinguish between a recording of brain waves and electrical field fluctuations occurring in nature. The frequency spectrum of a measured vertical electrical field of natural signals is reproduced in Toomey, J. and C. Polk; Research on Extremely Low Frequency Propagation with Particular Emphasis on Schumann Resonance and Related Phenomena; [University of Rhode Island, Kingston, R. I., USA; Contract No. AF 19 (628)-4950; Apr. 1, 1970].

FIG. 7 shows these measurements, wherein it is clear that the Schumann resonances are shown as typical resonance phenomena. If these values are then compared to those obtained through Fibonacci scaling, (see Table 1), it is clear that they are in agreement therewith. The Fibonacci scaling frequencies can only be compared, however, with the resonance frequencies of the undamped "earth-ionosphere cavity resonator" (D=0). Such a damping, D=0, does not occur in nature, however, such that there are deviations, particularly at the higher Schumann resonances, thus at frequencies above 22 Hz, although the first 3 frequency maximums are nearly identical. The "resonance value" at higher frequencies in particular, is relatively low:

| Schumann Resonance: | 8.4 | 14.2 | 20.7 Hz |
|---|---|---|---|
| | ↕ | ↕ | ↕ |
| Fibonacci Frequency scaling: | 8.225 | 13.31 | 21.53 Hz |

Because these frequencies are also typical EEG frequencies, (start and end of the alpha range and the beta range), and the latter are also decisive for the effects of pharmaceuticals, important conclusions can be drawn from these results regarding therapeutic procedures (including the magnetic fields according to the invention).

It is furthermore known from measurements of the earth's magnetic field that oscillations can occur with a range of variation in the lengths of the periods from 30 seconds (≡0.033 Hz) to 0.025 seconds (≡40 Hz). As a result, this bandwidth is identical to that of the electrical field and the EEGs as well as the Fibonacci scaling 34.84 Hz, such that it can be assumed that there is a clear redundancy in the electrical and magnetic fields. Oscillations with a period of 4.5 seconds (=0.22 Hz) were also noticed in the measurements of the earth's magnetic field, even though they only had an intensity of $10^{12}$ teslas. These components clearly correspond to the breathing rate, as demonstrated previously. Consequently, it can be concluded therefrom that the breathing in the human cardiovascular system is "supported" by the earth's magnetic field. The determined frequency value differs little from the determined optimum $f_4$=0.283 Hz on the basis of the Fibonacci scaling, such that it can also be assumed here that the model and reality are in very close agreement.

That the earth's magnetic field is generally subjected to temporal fluctuations, and that the quantitative Schumann resonances can also be derived from such recordings of measurement values, is known.

SUMMARY

Using the "fractal self-similarity" introduced by Mandelbrot, West and Goldberger, it has been demonstrated that the Fibonacci scaling with its limit value of 1.618034 . . . (golden ratio) represents a structural model for quantifying statistical values and parameters in the human cardiovascular system. If such a Fibonacci scaling is used as the basis for optimal performance and energy transfer from the heart to the peripheral vessels, then optimal values for the cardiac cycle/heart rate, breathing rate and blood pressure periodics can be determined, as well as for the EEG range, as therapy frequencies for the magnetic fields that are used. In this sense, the oxygen extraction from the tissue is also optimized. At the same time, characteristic relationships are obtained based on the limit value 1.618034, which arise between the statistical values and the parameters.

The derived optimal values, including relationships, are in close agreement with the known clinical standard values.

The model, "Fibonacci scaling with a limit value of 1.618034 . . . " can also apparently form the basis for the natural electromagnetic field. The frequency spectra obtained from the practical measurements of the natural electromagnetic field of the earth's ionosphere cavity resonator, particularly the Schumann resonances, are comparable to the EEG frequency ranges and the frequencies obtained by means of Fibonacci scaling. This also relates to the frequencies and ranges derived from measurements of the earth's magnetic field. The frequency comparison of the natural electrical field and the earth's magnetic field clearly indicates a redundancy, which has been and is clearly necessary for the development of life on our earth.

It has thus been proven with the above explanations that an improvement in the therapeutic effects can be obtained through the special frequency scaling of the magnetic fields that are used, which was not known so far.

The magnetic field applicator is preferably part of a treatment device for magnetic field therapy. The treatment device can be in the form of a treatment chair, and have one or more magnetic field applicators. Each magnetic field applicator comprises at least one treatment coil with a magnetic core, which are incorporated in the treatment device, and generate a magnetic field emitted from a surface, e.g. a seat, backrest, or footrest of the treatment device.

The magnetic field emitted from a surface of the treatment device has a spatial volume and forms a plateau surface in the x and y directions of the surface of the treatment device, which has a relatively homogenous magnetic flux density.

The subject matter of the present invention can be derived not only from the subject matter of the individual claims, but also from combinations of the individual claims.

All of the information and features disclosed in the documents, including the abstract, and in particular the spatial designs shown in the drawings, are claimed as substantial to the invention, insofar as they are novel with respect to the prior art, individually or in combinations thereof.

The invention shall be explained in greater detail below, based on drawings showing just one method of execution. Further features and advantages of the invention that are substantial to the invention can be derived from the drawings and the descriptions thereof.

Figure 13:
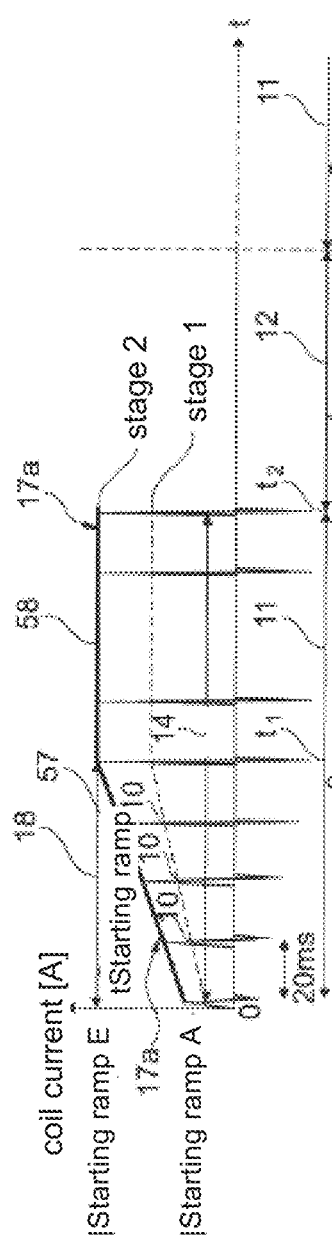
Figure 14:
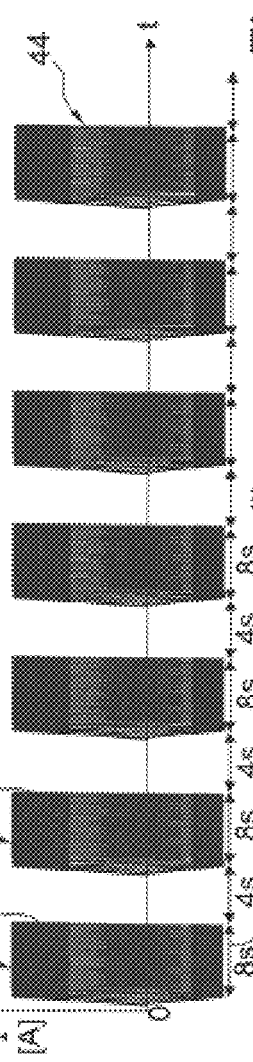
Figure 15:
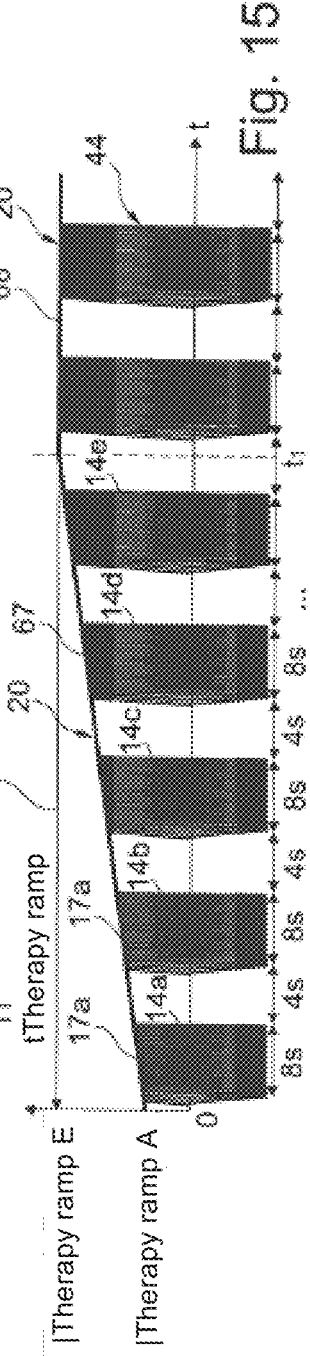
Figure 17:
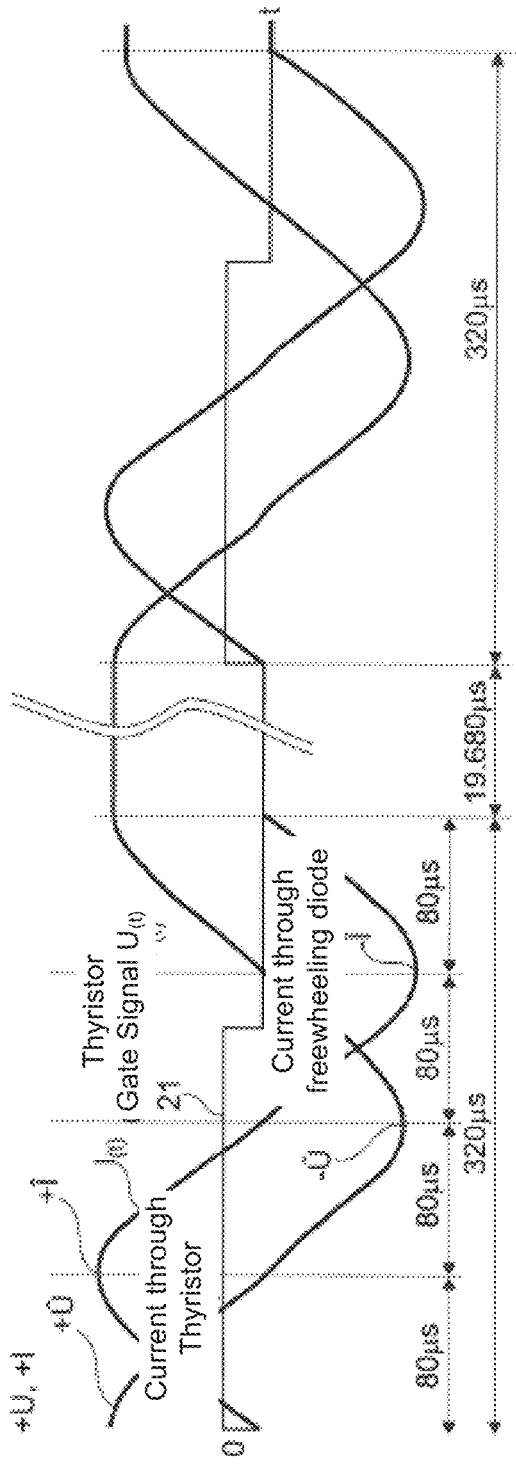
Figure 16:
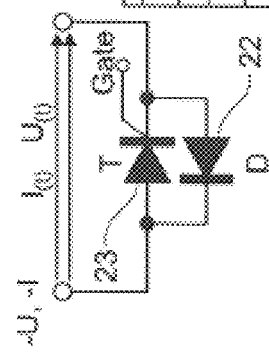

Therein:

FIG. 1: shows the relationship of the storage capacities (blood volumes) C of the venous and arterial systems FIG. 2: shows a distribution of blood volumes and blood flow resistance in the vascular system FIG. 3: shows resting blood pressure values in relation to the age of the subject, as well as the standard range for the ratio $RPW_1$ derived therefrom FIG. 4: shows a blood pressure profile as a function of the time of day FIG. 5: shows the ratio $RPW_1$ derived from FIG. 4 and the hourly mean value for the systolic and diastolic blood pressure FIG. 6: shows the number of branchings in the corresponding branching levels FIG. 7: shows the spectrum of natural signals of a vertical electrical field, including the characteristic Schumann resonances FIG. 8: shows a schematic illustration of a preferred treatment device FIG. 9: shows an illustration of the coil current according to the prior art FIG. 10: shows an illustration of the current pulses obtained from the individual coil currents according to the prior art FIG. 11: shows an illustration of the treatment blocks formed from the individual base pulses according to the prior art FIG. 12: shows an illustration of the invention in comparison with FIG. 3, with data from various ramp functions in a first embodiment FIG. 13: shows the same illustration as FIG. 12, with a different ramp function in a second embodiment FIG. 14: shows an illustration of the individual treatment blocks according to the invention, with base pulses in each case, which follow a ramp function FIG. 15: shows another embodiment of the depiction according to FIG. 14, in which the treatment blocks also follow a ramp function FIG. 16: shows an illustration of a thyristor/diode control, with a circuit according to FIG. 17

FIG. 17: shows an illustration of the thyristor/diode control

Figure 18:
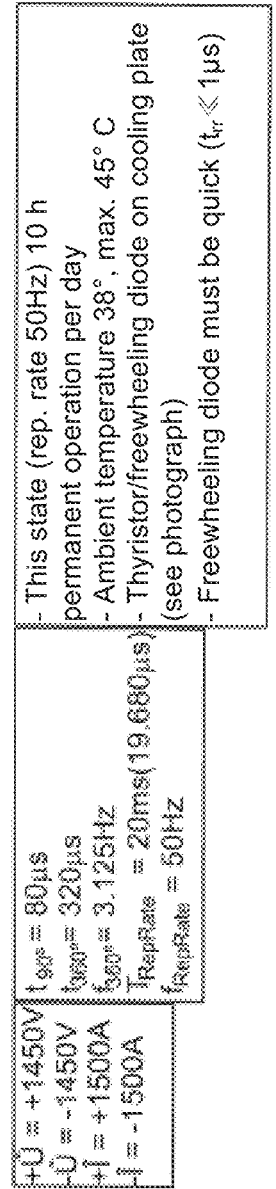

FIG. 18: shows the tables belonging to the drawings in FIGS. 16 and 17

Figure 19:
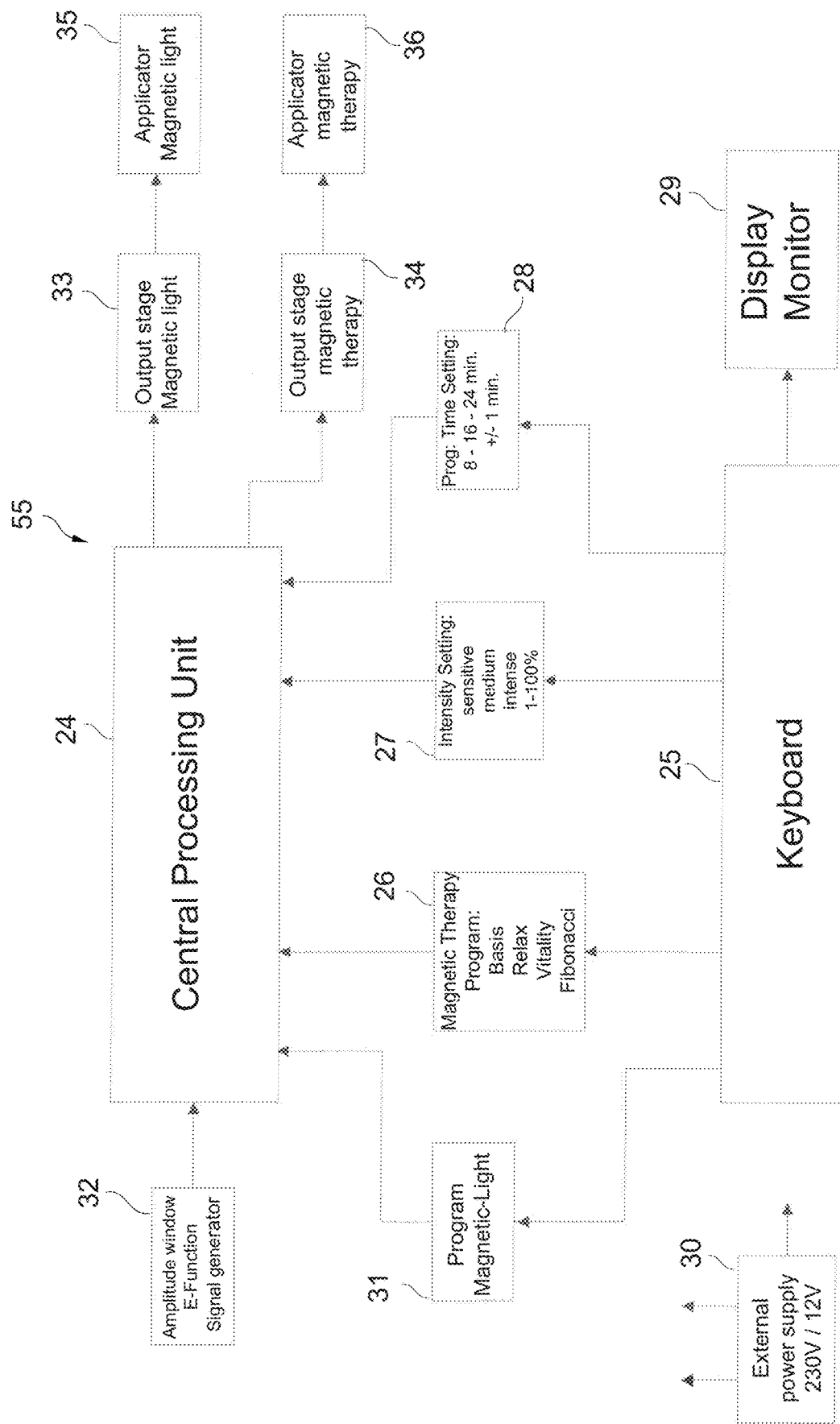
Figure 20:
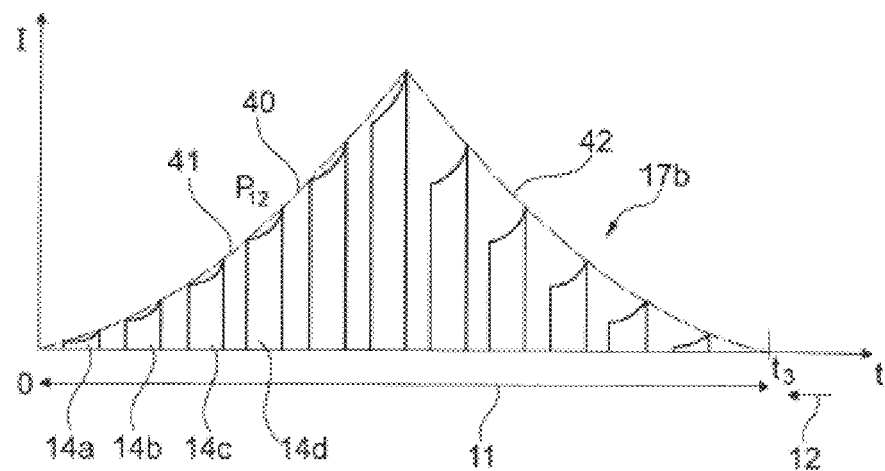
Figure 21:
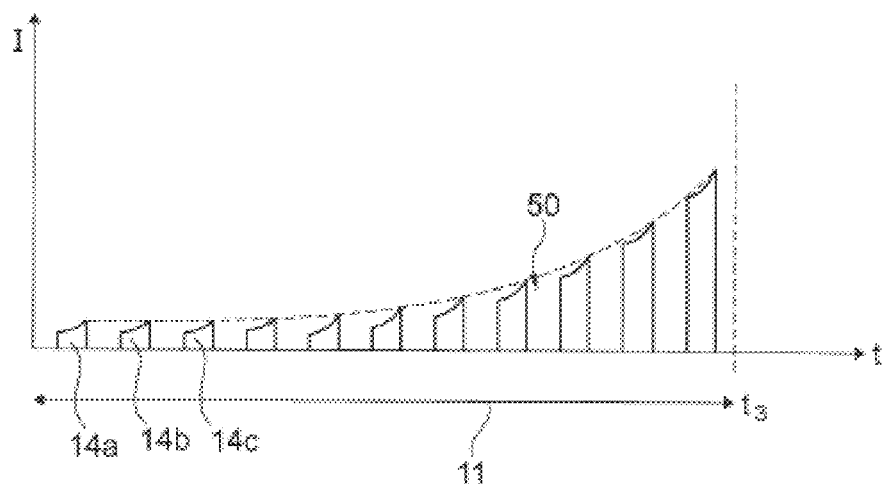

FIG. 19: shows a schematic block diagram of a treatment device with a depiction of the individual functional blocks FIG. 20: shows a depiction of that in FIG. 12, in a modified embodiment, in which a ramp function that increases and decreases in the manner of an exponential function within a treatment period is selected FIG. 21: shows a variation of FIG. 20, in which the ramp function corresponds only to a rising exponential function in the treatment period FIG. 22: shows the function of an envelope, which is later used to form the current pulse FIG. 23: shows a depiction of the trigger pulse, placed between the envelopes in FIG. 22

Figure 28:
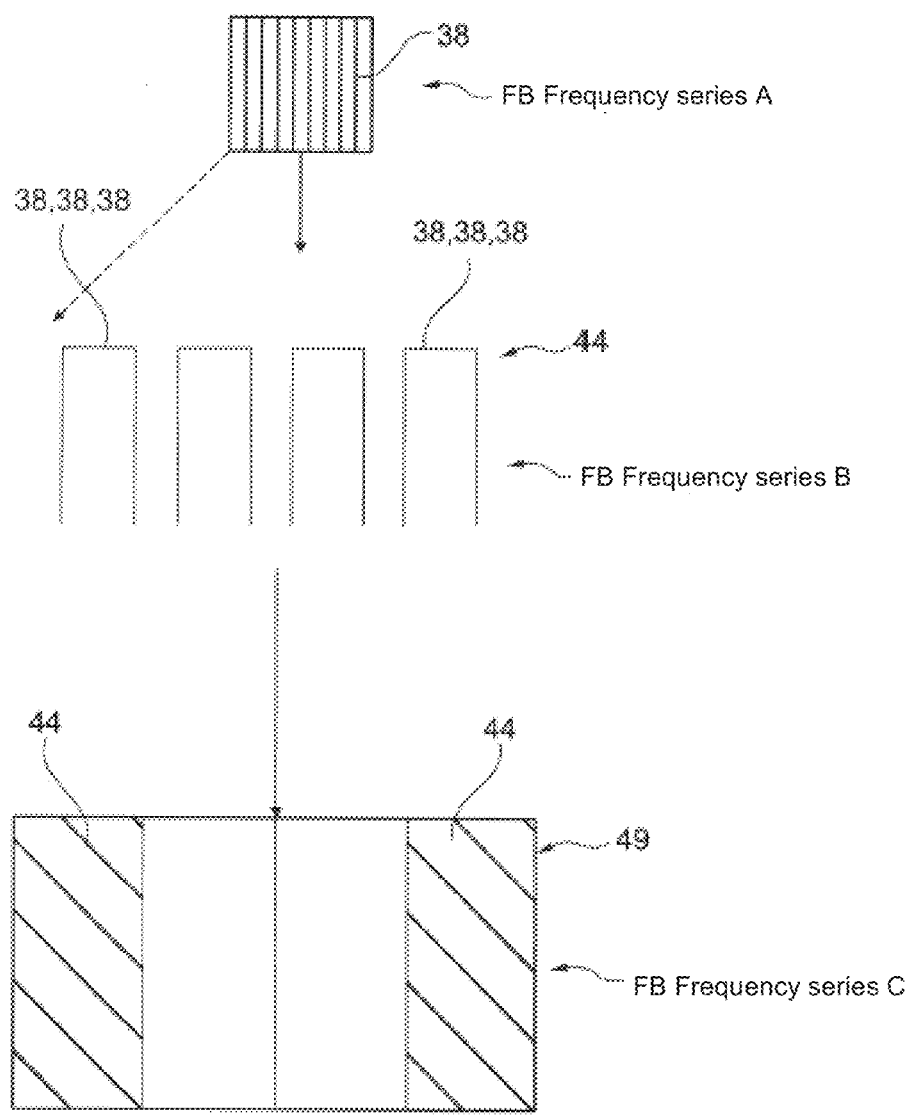
Figure 29:
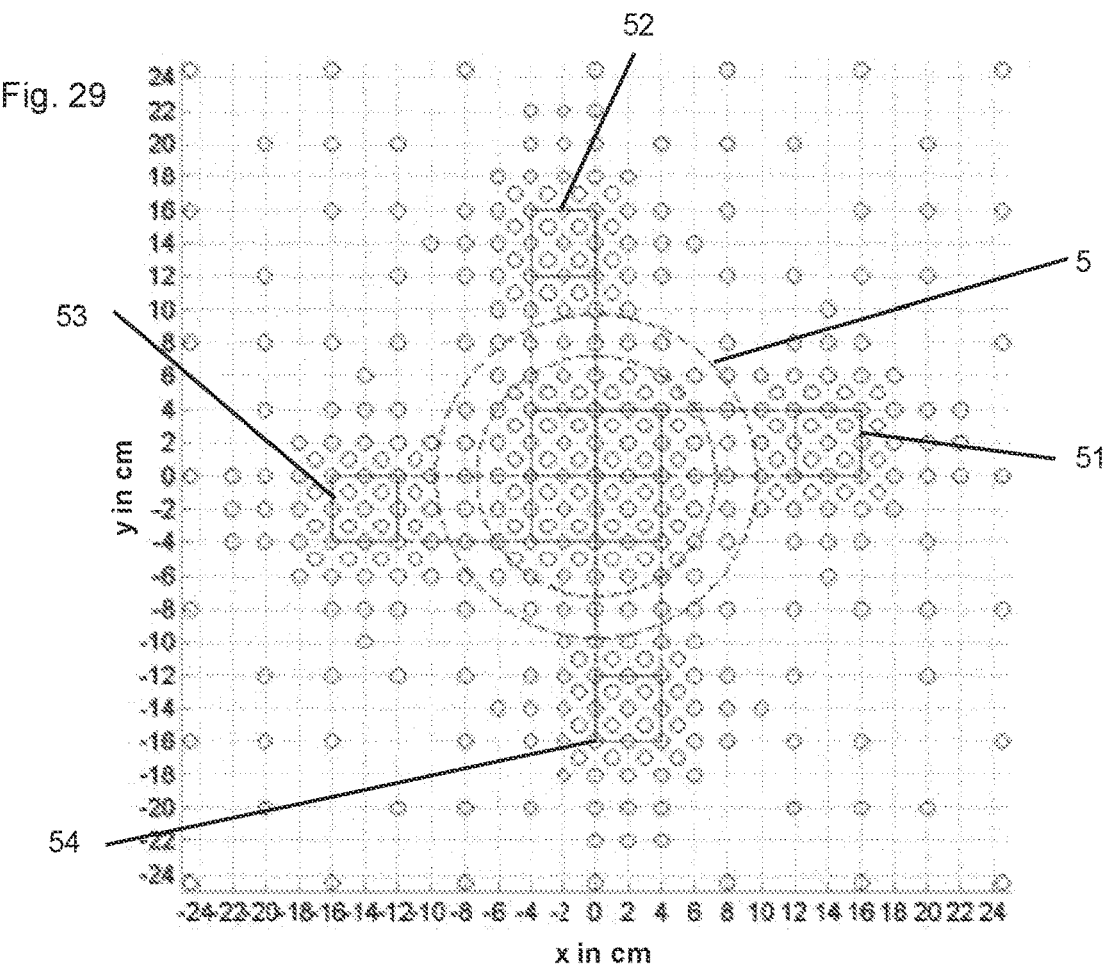
Figure 30:
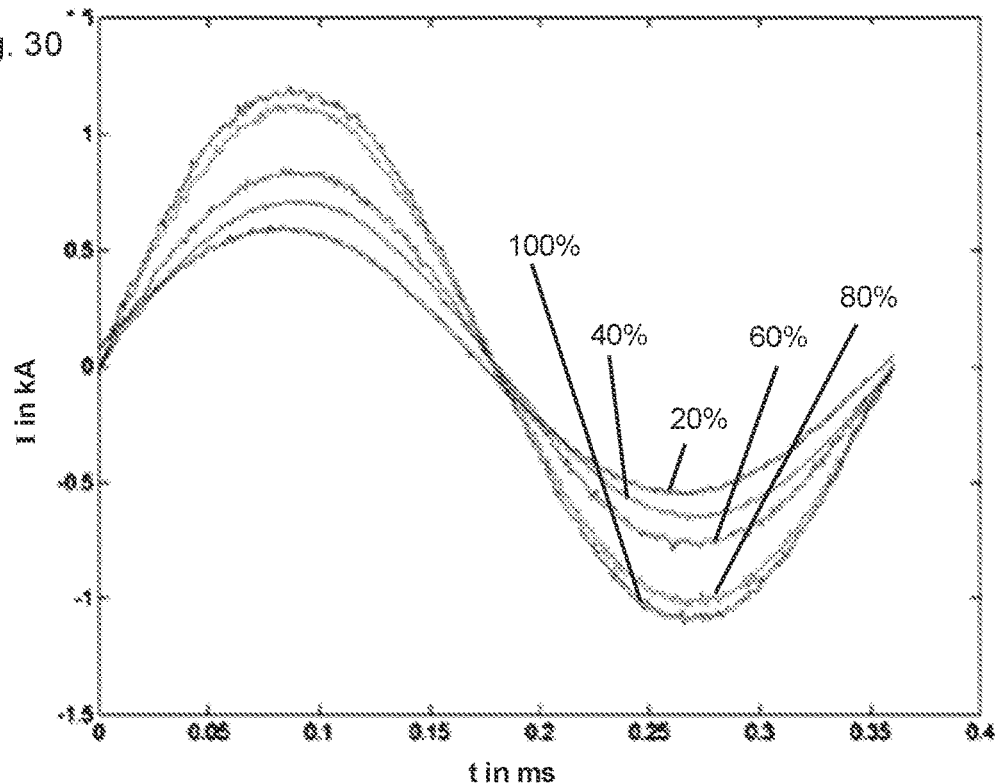

FIG. 24: illustrates how a number of base pulses are accommodated in the range of the envelope FIG. 25: shows how a number of treatment blocks with an envelope according to FIG. 24 are successively arranged in a specific frequency pattern FIG. 26: shows how this frequency patterns can be grouped together to generate a superimposed frequency FIG. 27: shows how the Fibonacci frequencies are distributed FIG. 28: shows a schematic illustration of how the treatment blocks formed by individual base pulses are combined to form large treatment blocks, and these in turn are combined to form further treatment blocks, which then follow a specific frequency pattern FIG. 29: shows the measurement point distribution in the x-y plane FIG. 30: shows the measured coil current at intensity settings of 20%, 40%, 60%, 80% and 100%

Figure 31:
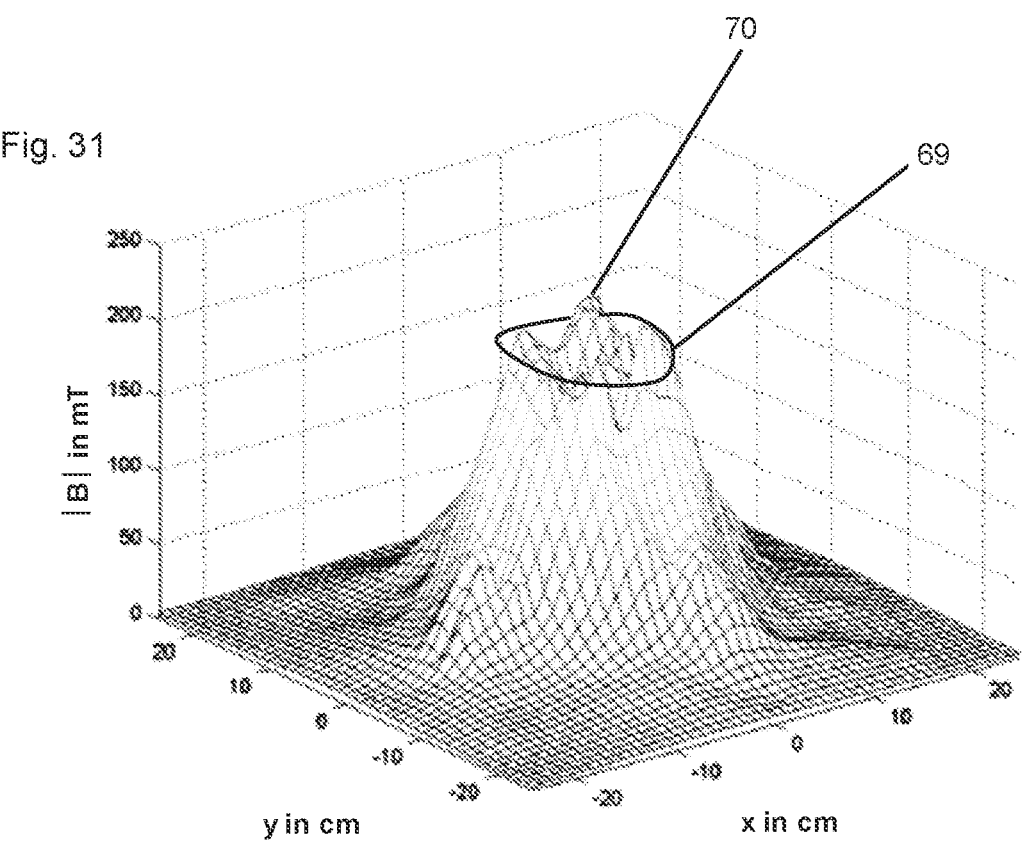

FIG. 31: shows the spatial distribution of the magnetic flux density in the seat plane (z=0)

Figure 32:
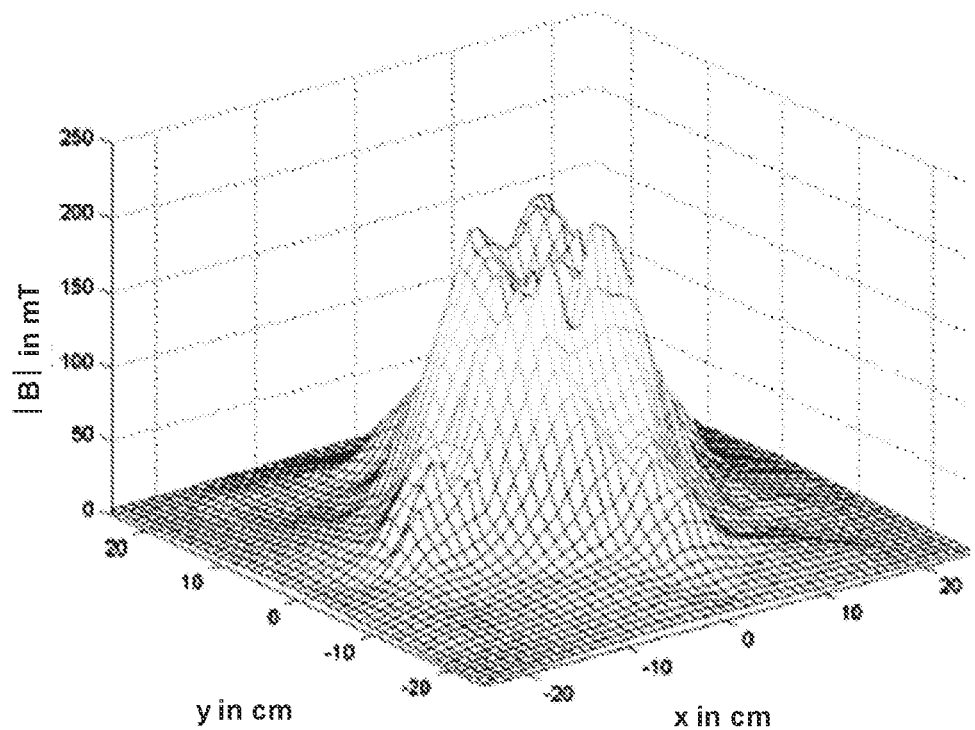

FIG. 32: shows the spatial distribution of the magnetic flux density in the pelvic floor plane (z=12 cm)

Figure 33:
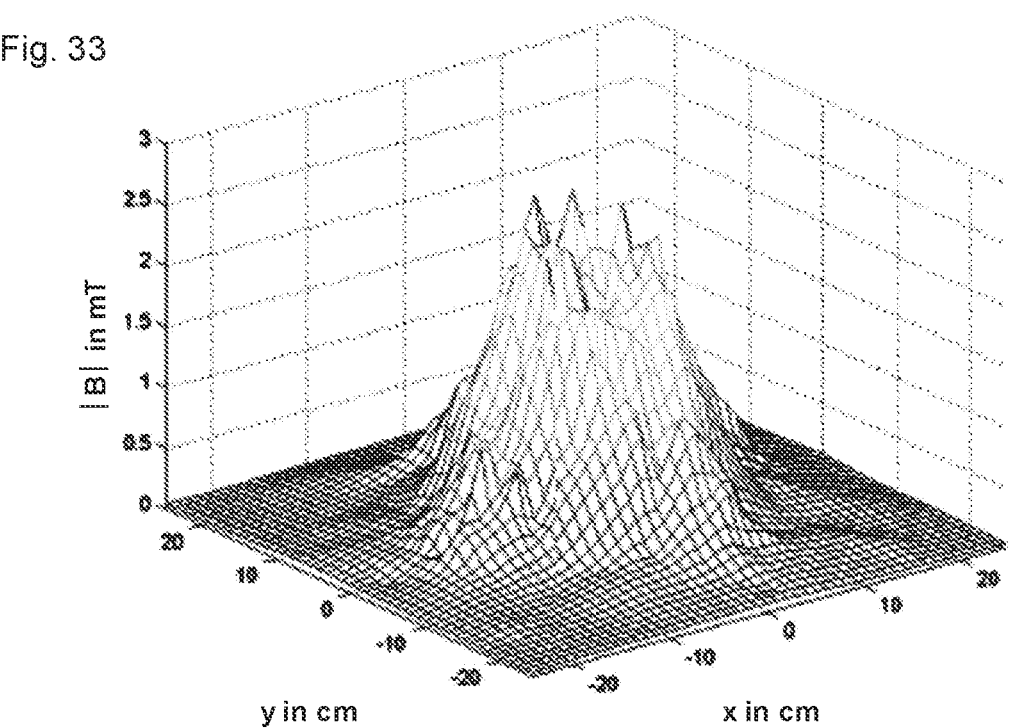

FIG. 33: shows the spatial distribution of the magnetic flux density in the heart plane (z=35 cm)

Figure 34:
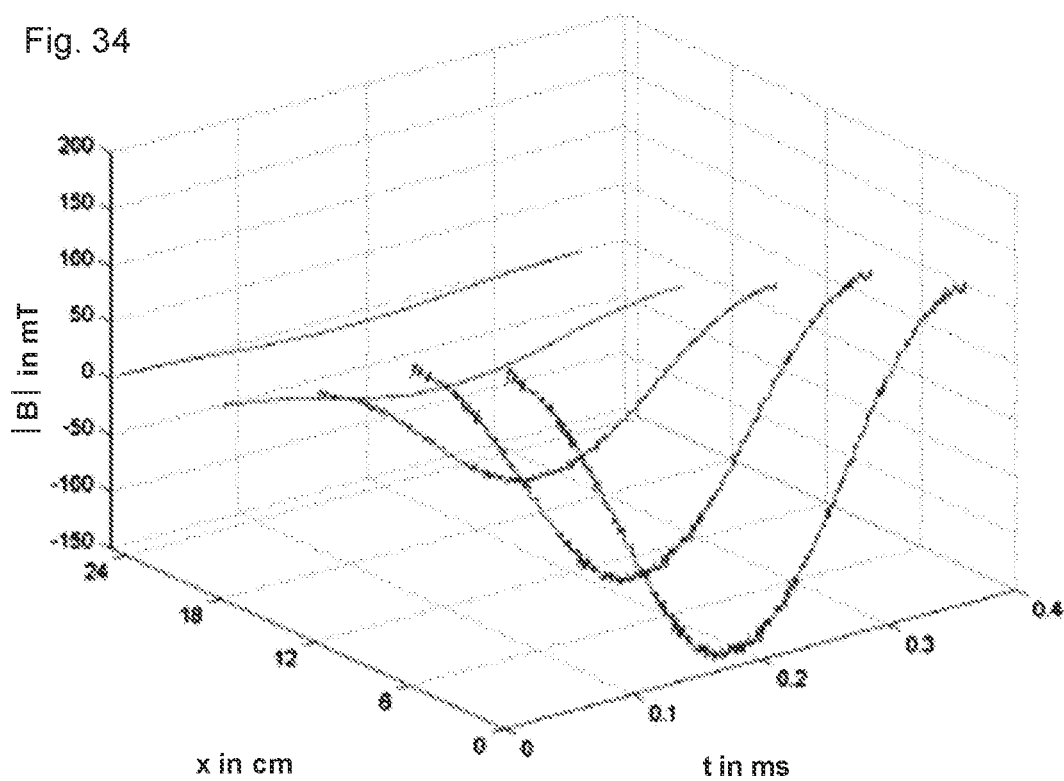
Figure 35:
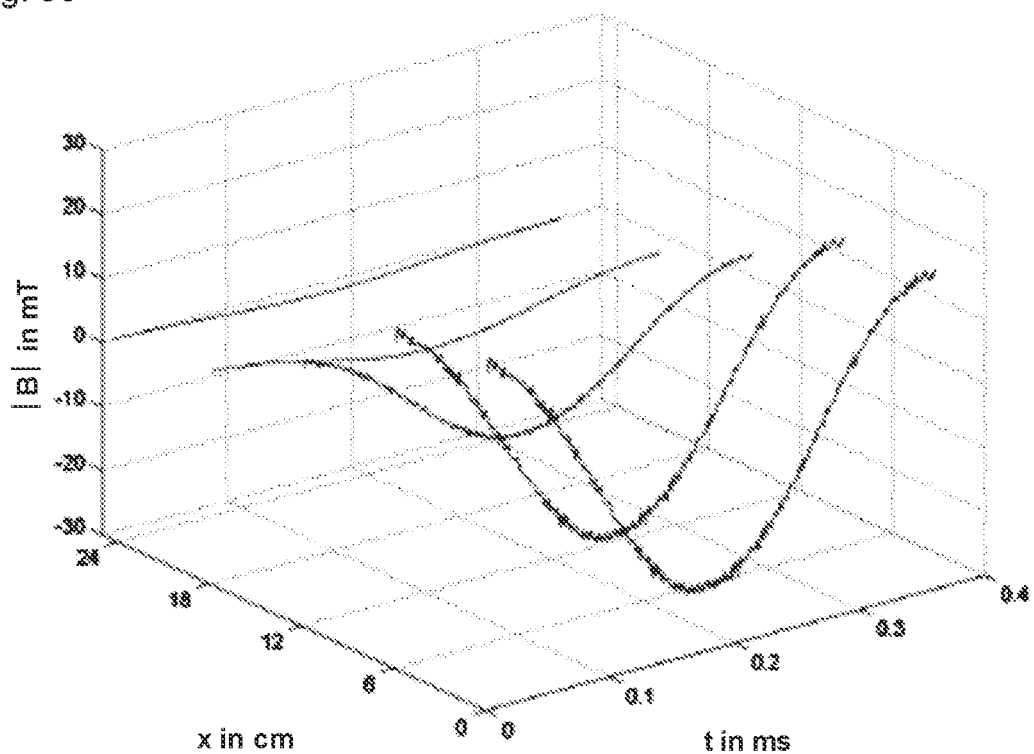
Figure 36:
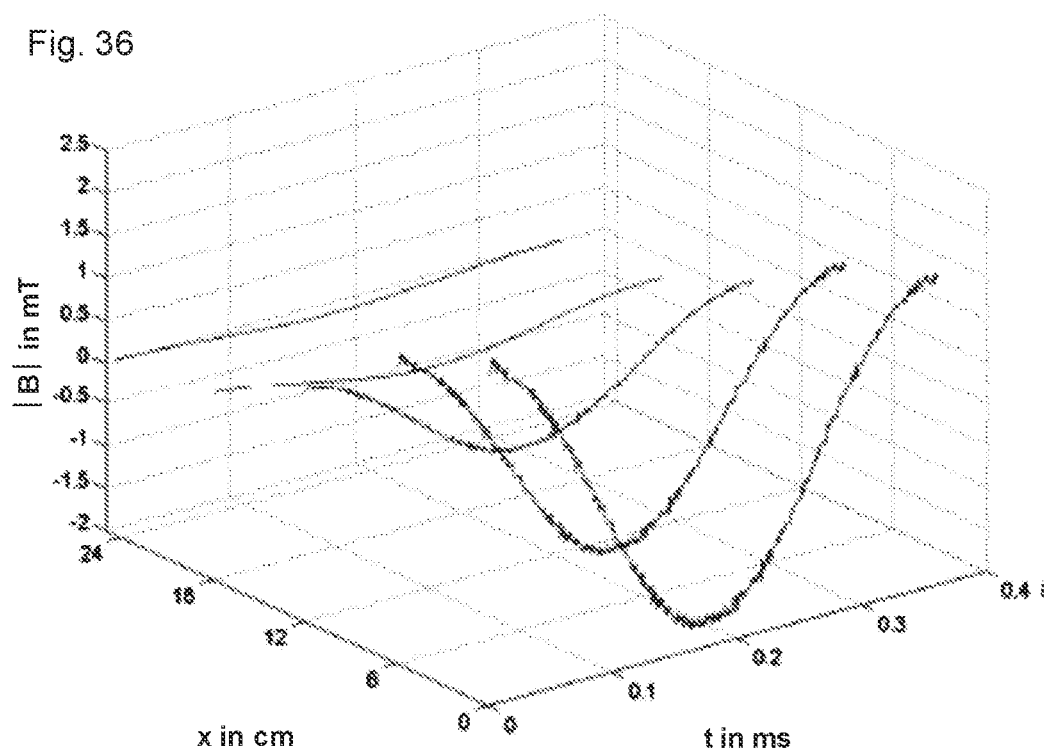
Figure 37:
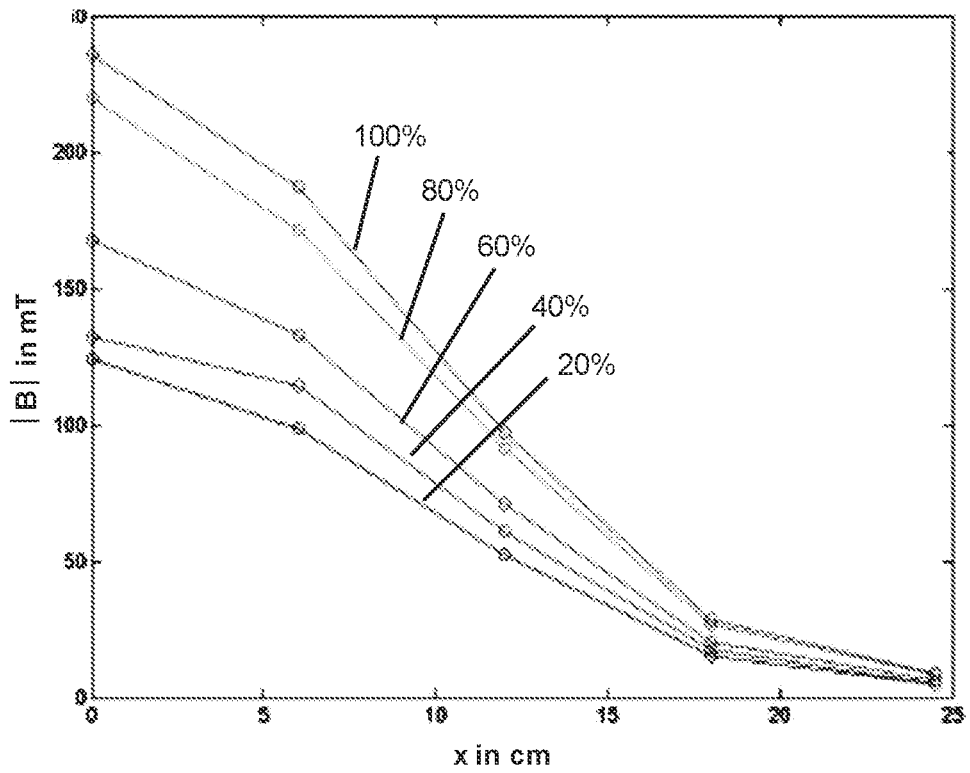
Figure 38:
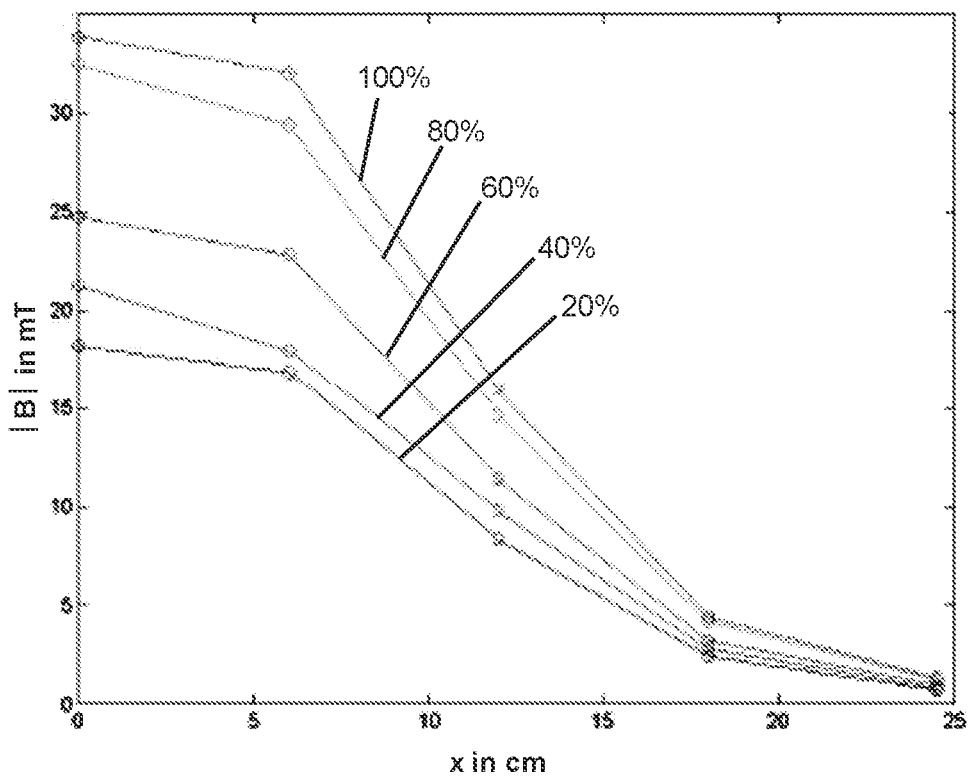
Figure 39:
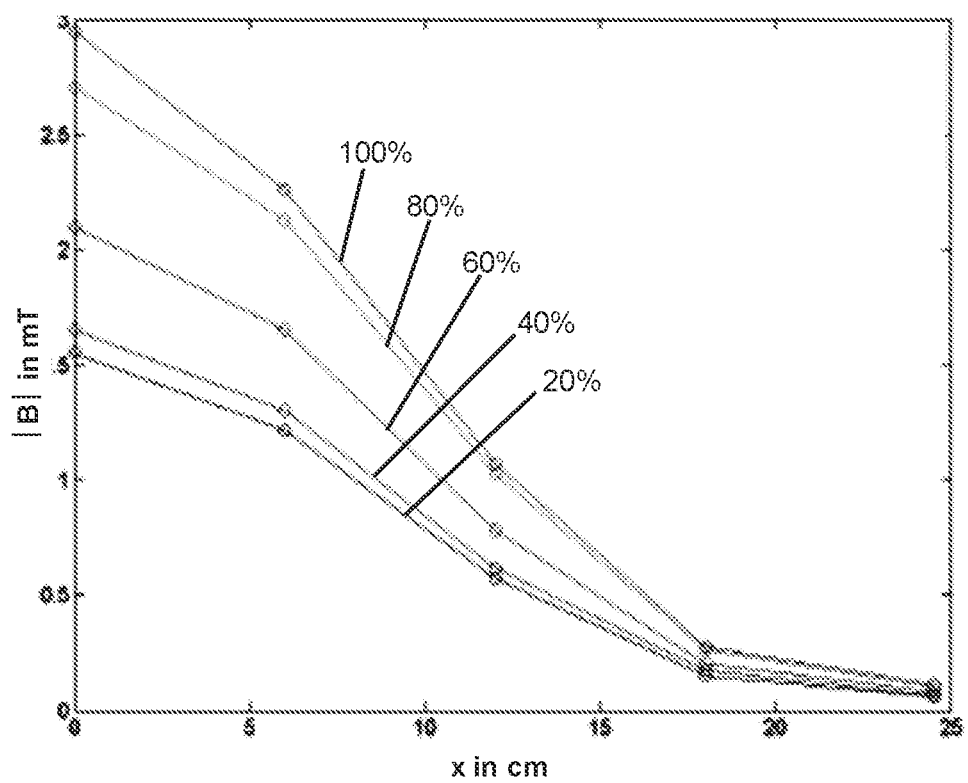
Figure 40:
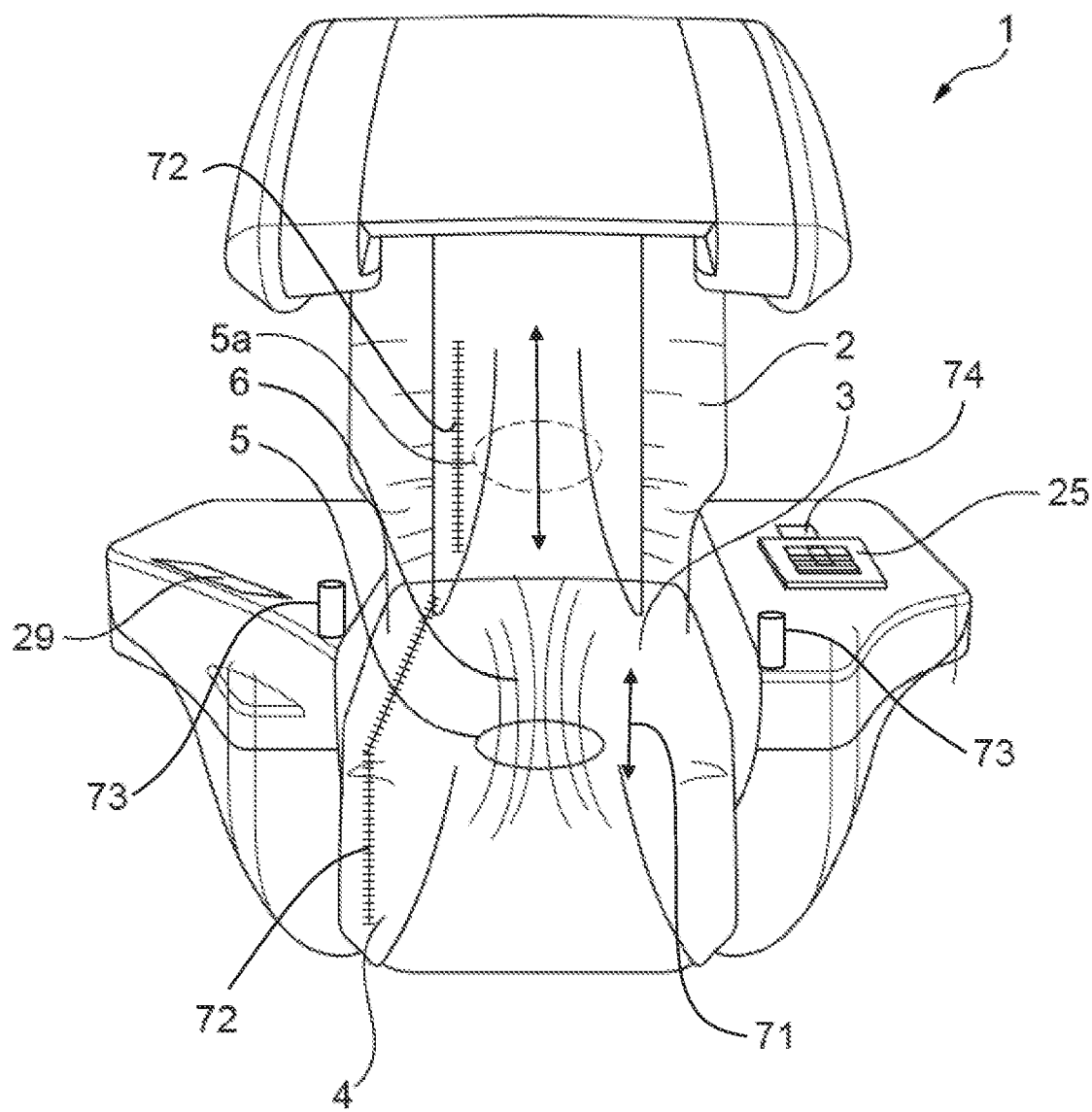

FIG. 34: shows the magnetic flux density (over time) in the seat plane (z=0) along the positive x axis at five measurement points FIG. 35: shows the magnetic flux density (over time) in the pelvic floor plane (z=12 cm) along the positive x axis at five measurement points FIG. 36: shows the magnetic flux density (over time) in the heart plane (z=35 cm) along the positive x axis at five measurement points FIG. 37: shows the magnetic flux density in the seat plane (z=0) along the positive x axis at five measurement points with different intensity settings FIG. 38: shows the magnetic flux density in the pelvic floor plane (z=12 cm) along the positive x axis at five measurement points with different intensity settings FIG. 39: shows the magnetic flux density in the heart plane (z=35 cm) along the positive x axis at five measurement points with different intensity settings FIG. 40: shows a schematic illustration of a modified design of a preferred treatment device.

The treatment device 1 shown in FIG. 8 is composed in the preferred exemplary embodiment of a treatment chair comprising on the whole a backrest 2, a seat 3 and a footrest 4.

The backrest 2 can be folded down, toward the back, from the seat 3, and the footrest 4 can be folded down or up, depending on which body part is to be treated on the treatment device 1.

The person being treated sits on the treatment device 1, which is in the form of a chair, and is irradiated with additional light sources from above that are generated by an applicator 35 in the upper surface of the backrest 2.

The illustration in FIG. 8 shows the location of a first possible treatment coil 5, which is located, by way of example, in the seat 3, and a suitable magnetic field 6, generating a maximum field strength of 1.6 tesla, for example, wherein the magnetic field 6 passes through the body part of the person sitting on the treatment device 1 that is to be treated, and triggers corresponding electrical potentials in the muscle fibers, in order to thus generate a periodic or aperiodic muscular contraction.

The muscle contractions take place through the nerves that enervate the muscle fibers, which are subjected to a stimulating voltage generated by the alternating magnetic field. This comprises a magnetic stimulation based on the Faraday principle, that an alternating magnetic field (temporally or spatially) generates a current flux in tissues. A depolarization of motor nerves and muscles occurs in the rhythm of the frequency switching, e.g. between 10-50 Hz in the effective field, resulting in consecutive strong contractions in the fasciated musculature. This is a result of releasing neurotransmitters at the motoric end plate.

The stimulation of afferent fibers of the stimulated nerves is regarded as an additive active principle.

In another embodiment of the treatment device 1, an additional treatment coil 5a can be placed in the backrest 2, additionally or in and of itself, or that, alternatively and optionally, an additional or single further treatment coil 5b can be placed in the footrest 4.

The treatment coils 5, 5a, 5b can also be designed such that they can be adjusted longitudinally in the treatment device 1, and can be displaced, and one or more treatment coils can also be eliminated, such that, e.g., just one treatment coil 5 is present in the seat, or just one treatment coil 5a is present in the backrest, or just one treatment coil 5b is located in the footrest.

One or more treatment coils 5, 5a, 5b can also be used as handheld treatment coils, i.e. they are held in the hand, and placed on a specific body part of the person being treated. Such applicators are disclosed in EP 0 594 655 B1.

The treatment device 1 is in the form of a chair in the drawing, although the invention is not limited thereto. The treatment device 1 can also be in the form of a bed, stool, or suchlike, and can have one or more coils.

It has also been shown that an additional light treatment also works well on the treatment device 1 with a suitable applicator 35.

As long as the magnetic fields 6 are functioning in one of the treatment coils 5, 5a, 5b, the light field generated by the applicator 5 also functions much more strongly, and the effects of the light field also increase the success of the therapy.

It has been shown that the effects of light at, e.g. 10,000 lux, used only for a light therapy, result in a treatment period of at least one hour. Tests have shown that when the light therapy is combined with magnetic field therapy with magnetic fields 6, treatment periods of just 10 minutes are sufficient for obtaining the same desired level of success.

Tests have also shown that the special effect of the positive effects of light therapy via the applicator 35 only result in success when the magnetic fields that are used follow a ramp function, as shall be explained in reference to FIGS. 12, 13, and 14.

Based on FIGS. 9 to 11, the fundamental function for generating the magnetic fields 6 shall be explained, as can be derived, for example, from the patent application EP 0 594 644 B1 by the same author.

It is shown in FIG. 9 that the coil current can be generated in two different stages, e.g. stage 1 and stage 2.

The two different stages correspond to the two different current strengths that can be set on the control device 55 for magnetic fields of two different strengths. The two different current strengths are also indicated in FIGS. 14 and 15.

The coil current 8 in stage 1 is just approx. 20% of the maximum coil current, while the coil current 7 in stage 2 corresponds to 100% of the coil current.

Accordingly, the intensity in FIG. 9 can be set with the treatment device shown in FIG. 19, wherein the coil current in the exemplary embodiment is active in periods 9 of 360 microseconds, and a pause is incorporated between each of the periods.

FIG. 10 shows that individual successive base pulses 10, lasting, e.g., 20 milliseconds, are generated from the base pulses 10 generated in FIG. 9 as the further prior art, and a total treatment time 11 of, e.g., 8 seconds, is obtained. After completion of the treatment period 11, there is then a pause 12 of, e.g., 4 seconds, followed by another treatment period 11 of 8 seconds.

The times given herein are to be understood as entirely exemplary, and do not limit the invention at all. It is also shown that the base pulses 10 occur successively, lasting 20 milliseconds. The invention is based, however, on the exemplary embodiment in FIGS. 9 to 11, and decisively improves the functions shown there.

It can be seen from FIG. 11 (prior art) that numerous base pulses 10 are formed from the individual base pulses 10 within the treatment period 11, which collectively form a treatment block 14, which takes place within the treatment period 11.

Numerous, e.g. 40 to 60, base pulses 10 are contained in such a treatment block 14.

This is the starting point for the invention, which provides in a first exemplary embodiment according to FIG. 12, that the individual base pulses 10 follow a specific envelope curve 17 as ramp-shaped rising base pulses 10*a*, 10*b*, 10*c*, 10*d* and 10*e* within a treatment period 11, which is a parabolic curve in the exemplary embodiment therein. The amplitudes of these successive base pulses 10*a-e* thus follow a parabolic curve.

In another embodiment, instead of a parabolic curve, the amplitudes can follow a straight line or an exponential curve, as shall be explained below in reference to FIGS. 20 and 21.

The important thing is that, starting from an initial value 16, which is relatively low, close to zero, the current strength and the magnetic field increase slowly, in accordance with the envelope 17, until reaching a higher end value 15.

1. The frequency of the base pulses generated during a treatment period (dwell time) are in a range of 1 Hz to 50 Hz.
2. The initial value of the first pulse of the base pulses that are used is in a range of 1% to 30% of the maximum amplitude.
3. The amplitude of the base pulses generated in the treatment period is approx. 90%-100% of the maximum amplitude.
4. The treatment period (dwell time) lies in a range of 1 second to 12 seconds, and the pauses therebetween lie in a range of 4 seconds to 12 seconds.

FIG. 13 shows a second preferred exemplary embodiment in comparison with FIG. 12, in which it can be seen that the envelope 17*a* only extends over a portion of the treatment period 11 as a rising curve segment 57, e.g. for only half of the treatment period 11, and that upon passing the midway point t1 in the treatment period, the maximum coil current is generated until the end of the treatment period 11 in the form of the constant curve segment 58.

As a result, only one rising starting ramp 18 in the form of the rising curve segment 57 is used, in which the envelope 17 is used, which can either be a parabolic curve—corresponding to the preceding description, or a straight line or an exponential function.

The advantage of this is that starting at time t1, until time t2—in the region of the constant curve segment 58—the entire coil current, and thus the maximum magnetic field are available, while in the time 0 to t1, a rising starting ramp 18 is used, in order to obtain a gradual increase in the magnetic field in the tissue. As a result, unpleasant tissue reactions no longer occur, and nervous disruption pulses no longer occur, that have a strong negative impact on the success of the treatment.

FIG. 14 shows that the numerous base pulses 10 form a treatment block 14 with their respective envelopes, corresponding to the curve segments 57, 58, and numerous treatment blocks 14 form a packet in FIG. 14, and these packets take place successively at the same amplitude in the embodiment according to FIG. 14. All of the base pulses shown in FIG. 13 thus form pulse packets with constant amplitudes, in which the base pulses 10, however, are obtained with increasing amplitudes, either according to FIG. 12 or 13.

Numerous treatment blocks 14, each of which comprises numerous base pulses 10, are combined accordingly to form pulse packets 44 according to FIG. 14. The temporal spacing 13 between the individual base pulses 10 is thus shrunken, and depicted as numerous successive pulse packets 44 in FIGS. 14 and 15. Both the pause 12 as well as the treatment period 11 can be set with the control device 55 shown in FIG. 19. The treatment period 11 extends with the pulse packets 44 over a period of 8 seconds in the exemplary embodiment shown therein, followed in each case by a pause of, e.g., 4 seconds.

In the exemplary embodiment according to FIG. 14, the envelope of the current amplitudes is a rectangular curve. With numerous ramp-shaped rising base pulses contained in each pulse packet 44, however, therapeutic success is achieved.

The base pulses 10, 10*a*, 10*b* that are used preferably have the following properties:
Envelope pulse shape (rectangular, exponential function, or sawtooth)

| | |
|---|---|
| Repetition frequency | (1 Hz-50 Hz) |
| Starting value first pulse | (1%-100%) |
| End value last pulse | (1%-100%) |
| Dwell time | (1 second-12 seconds) |
| Pause time | (4 seconds-12 seconds) |

The success of the therapy can be further increased when, instead of a rectangular envelope according to FIG. 15, a ramp-shaped rising envelope 20 is used.

This envelope 20 is comprised of a rising curve segment 67, the incline of which starts close to zero and extends over numerous treatment and pauses 11, 12. The rising curve segment 67 is also referred to as a "therapy ramp."

In a variation on FIG. 14, it is also shown in FIG. 15 that the individual amplitudes of the successive treatment packets 14 can follow an envelope 17 such that the individual successive treatment blocks 14*a*-14*e* follow a specific amplitude function, specifically a therapy ramp 19, formed by a rising envelope 20.

This envelope 20 can also be either a straight line or a parabolic or exponential function.

A gradual introduction of the individual treatment blocks 14 composed of base pulses is obtained, wherein numerous base current pulses 10 are contained in each treatment block 14, corresponding in each case to the envelope function according to FIG. 13.

FIGS. 16 and 17 show the technical execution of the current control according to the aforementioned FIGS. 13, 14, and 15.

It can be derived from FIG. 17 that a thyristor 23 is activated at its gate with a gate signal 21 according to FIG. 16, and an opposing polarized free-wheeling diode 22 is connected in parallel thereto.

Starting at the time 0, there is therefore a positive peak current of, e.g., 1500 amperes, which reaches the zero crossing at a specific time, after which a compensating current passes through the free-wheeling diode as a negative current of 1500 amperes.

The voltage curves in the coil are also indicated, as well as the preferred time periods that are in effect therein.

The various parameters are listed individually by their numerical values in FIG. 18 (table).

It should be emphasized that the numerical values represent only a preferred exemplary embodiment, and that the invention is not limited thereto.

The functional structure of such a control device 55 is shown in FIG. 19, wherein a signal generator 32 activates a digital central processing unit 24, with which the amplitude window and the envelopes 17, 20 are generated.

There is an input for a program selector 31 in the central processing unit 24, with which the light effect can be generated via the applicator 35. This is activated in turn by keyboard 25.

The keyboard 25 likewise activates a program selector 26, with which the various programs in the magnetic field therapy can be initiated.

In addition to the base program, there is also a relax program, a vitality program, and a Fibonacci program, in which a specific frequency distribution of the magnetic pulses is used according to the invention.

The keyboard 25 also activates an intensity selector 27, with which the intensity of the magnetic pulses can be controlled. There are various programs therein.

The keyboard 25 also activates a timer 28, and a power output stage 33 for the light therapy is activated at the applicator 35 in the output of the central processing unit 24, as well as a power output stage 34 for the magnetic field therapy, which is then sent to the applicator 36, which can be formed in the exemplary embodiment as a treatment device 1 with its coils 5, 5a, 5b.

There is also a power supply 30, and a display 29 for displaying the various functional states.

FIG. 20 shows a variation on the ramp function according to the invention in comparison with FIG. 12, in which another ramp function can also be obtained for the treatment blocks 14.

The amplitudes of the treatment blocks 14a, 14b, 14c, 14d increase therein in the manner of an exponentially rising curve segment 41 until reaching a midway point in the treatment, and decrease exponentially at the midpoint of the treatment period 11 in the form of another curve segment 42, until reaching the time t3. This is followed by the pause 12.

Instead of a starting ramp 18 with a slowly rising envelope 17, 17a, an exponential function can also therefore be used, which is comprised of a rising curve segment 41 and a falling curve segment 42.

In a variation on the exemplary embodiment according to FIG. 20, FIG. 21 shows that instead of rising and falling curve segments 41, 42, there can also be only a rising curve segment, and the envelope 50 formed by this can correspond to an exponential function.

FIGS. 22 to 27 show that all of the base pulses and the treatment blocks 14 formed by them follow a specific frequency pattern, which is referred to a Fibonacci frequency distribution.

There are numerous embodiments thereby, which shall now be explained below based on an exemplary embodiment.

The use of frequencies from the Fibonacci series allows for the following embodiments, wherein each exemplary embodiment can be combined with each of the other exemplary embodiments, or with numerous exemplary embodiments:

1. The use of one or more Fibonacci frequencies for forming the base pulses 10, 37 during the entire period of use or for a portion of the period of use.
2. The use of one or more Fibonacci frequencies for forming the pulse packets 44 formed by the base pulses 10, 37 during the entire period of use or for a portion of the period of use.
3. The use of one or more Fibonacci frequencies for forming the pulse packets 45, 49 formed by the pulse packets 44 during the period of use period or for a portion of the period of use.
4. The use of one or more Fibonacci frequencies for forming the frequencies of the successive pauses 39, 43, 47, 47 during the entire period of use or for a portion of the period of use.
5. The use of one or more Fibonacci frequencies for forming the frequencies of he successive treatment periods 10, 11, 44, 45, 49 during the entire period of use or for a portion of the period of use.

In this regard, FIG. 22 shows the ramp-shaped rising individual pulses 37 by way of example, which then are interrupted by trigger pulses lying therebetween according to FIG. 23. The individual pulses 37 correspond to the base pulses above.

The length of the individual pulse 37 in conjunction with the pause of the first pause lying between 4.5 and 5 seconds (packet spacing 46) and the pauses of 9.5 to 10 seconds in the second pause thus form a specific frequency sequence, which corresponds to a Fibonacci frequency.

It is shown in FIG. 24 that pulse packets 38 formed by the individual pulses 37 and the pauses from FIG. 22, in conjunction with the pauses lying therebetween, are formed with a specific successive frequency, specifically a frequency from the Fibonacci series, and the pulse packets 38 have a pause spacing 39, and are repeated periodically with a specific frequency from the Fibonacci series.

Concentrated pulse packets 44 are thus formed from the pulse packets 38 in FIG. 24, which also contain pauses lying therebetween (packet spacings 46, 47), and the even larger pulse packets 44 are formed therefrom, which in turn form even larger pulse packets 45 with pauses lying therebetween.

These form specific frequency patterns with the pauses, such as those shown in FIG. 25. The packet spacing 46 indicated therein corresponds to a specific pause. FIG. 26 shows the frequency distribution of the larger pulse packet 45 shown in FIG. 25, in an even denser concentration in the form of densely concentrated pulse packets 49.

The larger pulse packets 49 are formed therefrom accordingly, which in turn take place successively in accordance with at least one frequency of the Fibonacci series.

The pauses 4.5-5 and 9.5-10 seconds of the individual pulses 10, 37 shown in FIG. 22 are pauses corresponding to a Fibonacci distribution.

The pauses 0-136.5; 333.5 to XX shown in FIG. 25 are in turn pauses of a Fibonacci distribution FIG. 27 shows that the frequencies of the base pulses 10, 37 assume certain values, specifically in the time from 0 to t1, a frequency of 8.225 hertz, in the time t1 to t2, a frequency of 13.31 hertz, and in the time t4 to t5, a frequency of 21.53 hertz, etc.

FIG. 28 shows the nesting of the various pulse packets 38 to form larger pulse packets 44, and even larger pulse packets 49 in turn from these, which are formed in a specific Fibonacci frequency pattern.

The succession of this frequency pattern is explained in the general description.

FIG. 28 discloses numerous different embodiments using the frequency distribution according to Fibonacci (FB) for the frequencies that are used:

The base pulses 10, 37 correspond to a first FB distribution A

The pulse packets 44 formed by the base pulses 10, 37 correspond to a second FB distribution B The pulse packets 49 formed by the pulse packets correspond to a third FB distribution.

For these embodiments, the various possible frequency distributions and combinations thereof according to FB apply:

FB (A) and/or FB (B) and/or FB (C).

(1) This means that only the frequency of the base pulses 10, 37 can correspond to an FB distribution, but that the frequencies of the pulse packets 44 and 49 remains constant.

(2) This means that the frequencies of the base pulses 10, 37 can correspond to an FB distribution, that the frequency of the pulse packet 44 likewise corresponds to an FB distribution, but the frequency of the pulse packet 49 remains constant.

(3) This means that the frequencies of the base pulses 10, 37 can correspond to an FB distribution, but that the frequencies of the pulse packets 44 and 49 likewise corresponds to an FB distribution.

(4) Further embodiments can be derived from the further mutations of the aforementioned selection possibilities A and/or B and/or C The frequency distribution (A) can be the same as or different than the frequency distribution (B), which can be the same as or different than the frequency distribution (C).

It is thus clear that the specific frequency distribution of the base pule over time follows the Fibonacci frequency distribution, and that the success of the treatment with magnetic fields 6 in the treatment device 1 can be substantially increased.

The term, Fibonacci frequency distribution, refers in general to the frequencies listed in Table 1. Each of these frequencies can be used in and of itself for the frequency distributions (A) and/or (B) and/or (C). This means that each of the Fibonacci frequencies specified in Table 1 can be used as the frequency for the base pulses 10, 37 (distribution A) and/or for the frequency of the pulse packet 44 formed by the base pulses 10, 37, and/or for the pulse packets 49 formed by the pulse packets 44.

As a matter of course, it is also possible to use a first Fibonacci frequency (A) for the base pulses 10, 37, a second Fibonacci frequency (B) for the pulse packet 44, and a third Fibonacci frequency (C) for the pulse packet 49.

The term, "frequency distribution," therefore means that each arbitrary frequency (A and/or B and/or C) from the Fibonacci frequency series can be used in each arbitrary distribution (size) for the base pulses 10, 37 and/or the pulse packets 44 and/or the pulse packets 49 formed therefrom.

These frequencies can also correspond to the Fibonacci frequency scaling: 8.225 13.31 21.53 Hz.

It is advantageous when all of the pulses 10, 37 used herein and the pulse packets 44 and 49 formed therefrom have a ramp-shaped incline, as is depicted in FIGS. 13 to 15. Reference is made to the description therein.

As a result, the advantage is obtained, that the Fibonacci pulses (i.e. pulses 10, 37, and pulse packets 44 and 49, with the respective selected Fibonacci frequency A, B, C) that are particularly physiologically compatible and effective, will result in an improved therapeutic effect with shorter treatment times.

It has already been stated in the general description—in conjunction with Table 1—that the distribution of the intensities of the magnetic fields corresponding to the Fibonacci frequency scaling has major effects on the heart rate.

As a result, when the Fibonacci frequency scaling is used, both the heart rate, the efficiency of the blood circulation, the filling volume of the pericardium, and other physiological parameters of the circulatory system can be positively effected, as well as the effects of currents in the other bodily organs.

The Zentralinstitut für Medizintechnik [Central Institute for Medical Technology] of the Technischen Universität München [Technological University of Munich] has measured magnetic flux densities at various coordinates for the treatment chair 1 shown in FIG. 8.

This is a treatment chair 1 that is used, e.g., for incontinence treatments. The principle of the treatment substantially comprises repetitive, magnetic stimulation of the pelvic floor muscles. The methodology substantially corresponds to the established transcranial magnetic stimulation.

The measuring comprised measuring the magnetic flux density|B| in teslas at various coordinates, and measuring the time dependent coil current of the excitation coil.

The following measurement planes were established:
- 400 measurement points at the level of the seat (z=0) at an intensity of 60%
- 400 measurement points at the level of the pelvic floor (z=12 cm) at an intensity of 60%
- 400 measurement points at the level of the heart (z=35 cm) at an intensity of 60%
- 1 measurement point at the level of the brain (x=0, y=0, z=65 cm) at an intensity of 60%
- measurement of the coil current over time at intensities of 20%, 40%, 60%, 80% and 100%
- measurement of the magnetic flux density over time at an intensity of 60% at the 5 measurement points where y=0 and z=0, z=12 cm, and z=65 cm All of the measurements were carried out at a stimulation frequency of 5 Hz. Coordinate System FIG. 29 shows the distribution of 400 measurement points in the x-y plane, e.g. at the level of the seat 3 of the treatment chair 1 in FIG. 8. The broken lines show the position of the excitation coil, corresponding to the treatment coil 5 of the treatment chair 1, and the horizontal leg of the four U-shaped magnetic cores 51, 52, 53, 54. The solid lines indicate the positions of the frontal pole surfaces of the magnetic cores 51-54. The grid is selected irregularly on the basis of the geometry of the existing magnetic cores in the x and y directions.

The treatment coil 5 has an annular geometry, and is connected to an electrical power supply unit, e.g. the control device 55 described above, by means of which a suitable current signal can be applied to the coil 5 to generate transient magnetic fields.

The treatment coil 5 is preferably in the shape of a torus. There are four U-shaped magnetic cores 51-54 distributed over the circumference of the treatment coil 5, offset at 90°, or rotated 90° in relation to one another. Each of these magnetic cores 51-54 has a square or rectangular cross section. All of the magnetic cores 51-54 have a substantially planar pole surface on their upward extending legs.

The planar pole surfaces of the individual cores 51-54 all lie in a plane in the exemplary embodiment that can coincide with the plane of the treatment coil 5. Because one of the upward extending end sections of the magnetic cores 51-54 lies within the treatment coil 5 in each case, each magnetic core 51-54 forms a magnetic north pole or south pole at its end sections, following the flux direction, while the end sections lying outside the treatment coil 5 form a magnetic south pole or north pole, respectively. Accordingly, there are curved magnetic field lines running between the planar end sections.

The assembly, comprising the treatment coil 5 and the magnetic cores 51-54, is located beneath the seat 3 of the treatment chair 1, by way of example. As a result, the magnetic fields at the exposed end sections of the magnetic cores 51-54 penetrate relatively deeply into the biological tissue of a patient that is to be treated.

Measurement Equipment

The following measurement instruments are used for measuring the magnetic flux densities:
current probe i3000s, Fluke, Germany
Oscilloscope Wave Surfer 44 MXs, Le Croy, USA
DSP Gaussmeter 455, LakeShore, USA
Axial probe HMNA-1904-VR, LakeShore, USA
Transversal probe HMNT-4E04-VR, LakeShore, USA
Pick-up coil, IND-001, TUM, Germany The measurement equipment is calibrated in accordance with the directions of the manufacturers. In particular, the probes for measuring the magnetic fields were also calibrated thermally.

Executing the Measurements

First, the leather cushion is removed from the treatment chair 1, and the cover on the stimulation unit is detached. The current in the treatment chair 1 is subsequently measured with a current probe at intensities of 20%, 40%, 60%, 80% and 100%, with a repetition frequency of 5 Hz.

Subsequently, the cushion is replaced, and the magnetic flux density is measured three dimensionally at each coordinate (FIG. 29) in each plane (z=0 cm, z=12 cm, z=35 cm). The flux density is calculated from the contributions of the individual directional components:

$$|B| = \sqrt{B_x^2 + B_y^2 + B_z^2} \quad (13)$$

Over 100 stimulation pulses of the maximum magnetic flux density were established in order to determine the amplitudes of the magnetic flux densities B at each coordinate.

The error occurring in the positioning of the probes and through the measurement process was determined with all of the probes over a period of 20 seconds (this corresponds to 100 stimulation pulses at a repetition frequency of 5 Hz). The mean error was approx. 2% of the maximum. The error distribution was tested on a standard distribution using the Shapiro-Wilk test (S. S. Shapiro, M. B. Wilk, "An Analysis of Variance Test for Normality (Complete Samples)," Biometrica, Vol. 52, Nos. 3-4, pp. 591-611). Errors in the measurement results were eliminated on the basis of the standard distribution of this error.

Measuring the Coil Current

FIG. 30 shows the measured coil current of the treatment coil 5 at the intensities of 20%, 40%, 60%, 80% and 100%. The coil current has a damped sinusoidal curve over time.

The current curve over time is defined by the function $$I(t) \propto \sin(2\pi f \cdot t) e^{-\delta t} \quad (14)$$

In order to determine the lengths of the stimulation pulse, the oscillation frequency and the system damping, the measurement values are fitted to formula 14. The least squares method is used for this. Accordingly, the length of a stimulation pulse can be ca. 360 µs. This pulse length corresponds to an oscillation frequency f=2777 Hz. The system damping δ is 499. The system damping is obtained substantially from the ohmic losses in the coil lines. These parameters are not dependent on the intensity.

Three Dimensional Distribution of the Flux Density

FIGS. 31 to 33 show the spatial distribution of the magnetic flux densities in milliteslas, at an intensity of 60% in various planes.

FIG. 31 shows the spatial distribution of the magnetic flux densities in the seat plane (z=0). FIG. 32 shows the spatial distribution of the magnetic flux densities in the pelvic floor plane (z=12 cm). FIG. 33 shows the spatial distribution of the magnetic flux densities in the heart plane (z=35 cm). It is clear that the magnetic flux densities increase relatively steeply, and form a large effective surface with a relatively constant flux density at the maximum.

As a result of the U-shaped magnetic cores 51-54 of the treatment coil 5, the magnetic field has a pronounced spatial volume, i.e. it is in the shape of a pyramid, and fills a plateau surface (69) in the x and y directions with a relatively homogenous flux density. As a result, the magnetic field can penetrate deeply, and over a large area, into the tissue of the patient with a uniform flux density. The magnetic flux density in this plateau surface 69 is at least 85% of the current peak value 70 of the magnetic flux density.

The distribution of the flux densities over the surface is nearly identical in the measurement planes that were tested according to FIGS. 31 to 33, wherein only the maximum intensity decreases when the distance along the z axis to the seat 3 is increased.

Flux Density at the Level of the Head

The magnetic flux density at the level of the head was measured directly in the center at (x/y/z)=(0/0/65 cm). The maximum flux density is determined at a stimulation intensity of 60% for 0.11 microteslas.

Dynamic Measurement of the Magnetic Flux Densities

FIGS. 34 to 36 show the course of the magnetic flux densities over time along the positive x-axis at five exemplary coordinates where y=0, and which an intensity of 60%. The curves likewise follow the relationship according to Formula 14. The recording time window, however, is offset 90° to the depiction in FIG. 31. The damping and the oscillation frequency correspond to that of the current.

FIG. 34 illustrates the magnetic flux densities (over time) in the seat plane (z=0) along the positive x-axis at five measurement points. FIG. 35 illustrates the magnetic flux densities (over time) in the pelvic floor plane (z=12 cm) along the positive x-axis at five measurement points. FIG. 36 illustrates the magnetic flux densities (over time) in the heart plane (z=35 cm) along the positive x-axis at five measurement points.

Relationship Between Intensity and Magnetic Flux Density

FIGS. 37 to 39 show the measured values for the magnetic flux densities at five exemplary measurement points along the positive x-axis where y=0, for the seat, pelvic floor, and heart planes, at various intensities (20%, 40%, 60%, 80%, and 100%).

FIG. 37 illustrates the magnetic flux densities in the seat plane (z=0) along the positive x-axis at five measurement points at different intensities. FIG. 38 illustrates the magnetic flux densities in the pelvic floor plane (z=12 cm) along the positive x-axis at five measurement points at different intensities. FIG. 39 illustrates the magnetic flux densities in the heart plane (z=35 cm) along the positive x-axis at five measurement points at different intensities.

Relationship Between Coil Current and Repetition Rate

Table 2 shows the measured maximum coil currents at intensities of 20%, 40%, 60%, 80% and 100% with repetition frequencies of 5 Hz, 10 Hz and 30 Hz.

Table 3 compares the deviations in the current at 10 Hz and 30 Hz with the frequency 5 Hz (just the deviations of the means). As a result, the magnetic flux densities can be calculated for other intensities and frequencies.

TABLE 2

Maximum coil current at various intensities and at various frequencies.

| Intensity (%) | 5 Hz (90 pulses) | 10 Hz (120 pulses) | 30 Hz (360 pulses) |
| --- | --- | --- | --- |
| 20% | 600 A ± 3.2 A | 610 A ± 18 A | 610 A ± 17.7 A |
| 40% | 730 A ± 3.3 A | 740 A ± 20.2 A | 700 A ± 19.7 A |
| 60% | 880 A ± 8.9 A | 830 A ± 17.9 A | 800 A ± 19.8 A |
| 80% | 1180 A ± 20.7 A | 1180 A ± 31.6 A | 1060 A ± 20.7 A |
| 100% | 1250 A ± 16.9 A | 1220 A ± 17.4 A | 1220 A ± 29.4 A |

TABLE 3

Deviation of the maximum current at 10 Hz and 30 Hz from the current at 5 Hz.

| Intensity (%) | 10 Hz | 30 Hz |
| --- | --- | --- |
| 20% | +2% | +2% |
| 40% | +1% | −4% |
| 60% | −6% | −9% |
| 80% | ±0% | −10% |
| 100% | −2% | −2% |

FIG. 40 shows a schematic illustration of a modified embodiment of a preferred treatment device 1. The functions of the treatment device 1 can be tailored to the patients, wherein the corresponding treatment data for controlling the treatment coils 5, 5a for the magnetic field therapy, the applicators 35 for the light therapy (cf. FIG. 8), and, optionally, an additional oxygen generator for oxygen therapy can be stored on a personalized chip card 74 or similar element. The light therapy is used in particular for treating depression and the oxygen therapy is implemented for an additional promotion of muscle development. The treatment data, parameter settings, and measurement values stored on the chip card 74 can be displayed to the user, or the therapist, on the display 29 of the device at any time.

In contrast to FIG. 8, there is only one treatment coil 5 in the region of the seat 3 and the footrest 4, which can be displaced, however, along the seat 3 and the footrest 4 in the direction of the arrow 71. As a result, the treatment coil 5 can be moved to the region of the body that is to be treated in a targeted manner, e.g. into the region of the pelvic floor, the thigh, or the calf.

In order to be able to reproduce the optimal position of the treatment coil 5 after it has been set once, there is a scale 72 running along the seat 3 and the footrest 4, which comprises corresponding numerical values. The position of the treatment coil 5 is indicated on the scale 72 after it has been set, e.g. by means of an indicator light. Alternatively or additionally, the position of the treatment coil 5 can be displayed on the display of the treatment device after it has been set, e.g. through a numerical value or a graphical display.

Accordingly, the treatment coil 5a in the backrest 2 can likewise be displaced along the direction of the arrow, wherein the position is either indicated on a scale 72 along the backrest 2 and/or on the display 29, after it has been set.

The desired position(s) of the treatment coils 5 and 5a are preferably saved on the personalized chip card 74 of the patient. When the patient is identified with his chip card 74 on the treatment device 1, the personalized settings of the treatment device 1 are registered, and the treatment coils 5, 5a move automatically to the individual positions stored on the chip card 74. These positions can, of course, be changed at any time, and then saved again on the chip card 74.

The magnetic field strength is automatically reduced in the treatment coil 5a located in the backrest 2 as soon as the treatment coil 5a enters the region of the patient's heart, and this is set and programmed on the chip card 74 in the first treatment by a therapist. The chip card is therefore non-transferrable. The treatment cycle normally comprises 10 to 20 treatments.

Handles 73 can be placed on both sides of the treatment device 1, which are merely schematically illustrated in FIG. 40. The handles 73 are preferably ergonomic, and located such that the person sitting on the treatment device 1 can pull on the handles 73. The force exerted on the handles 73 is measured by measurement recorders in the handles 73, and displayed on the display 29 of the treatment device 1, and recorded, for example, on the personalized chip card 74 for a subsequent evaluation. As a result, a patient's increase in strength can be recorded and documented in the magnetic field treatment.

LIST OF REFERENCE SYMBOLS

1 Treatment device
2 backrest
3 seat
4 footrest
5 treatment coil
5a treatment coil
5b treatment coil
6 magnetic field
7 coil current (stage 2)
8 coil current (stage 1)
9 period
10 base pulse
10a base pulse
10b base pulse
11 treatment period
12 pause
13 temporal spacing (of 10)
14 treatment block
15 end value
16 initial value
17 envelope (parabolic)
17a envelope
17b envelope
18 starting ramp
19 therapy ramp 20 envelope (large)
21 gate signal
22 freewheeling diode
23 thyristor
24 central processing unit
25 keyboard
26 program selector
27 intensity selector
28 time setting
29 display
30 current supply
31 program selector
32 signal generator
33 power output stage
34 power output stage
35 applicator
36 applicator
37 individual pulse
38 pulse packet
39 spacing
40 envelope (large)
41 rising curve segment
42 falling curve segment
43 pulse spacing
44 pulse packet (large)
45 pulse packet (large)
46 packet spacing (large)
47 packet spacing (small)
48 frequency series
49 pulse packet
50 envelope (large)
51 magnetic core
52 magnetic core
53 magnetic core
54 magnetic core
55 control device
57 curve segment (rising) FIG. 13
58 curve segment (constant) FIG. 13
59 curve segment (rising) FIG. 15
68 curve segment (constant) FIG. 15
69 plateau surface
70 peak value (flux density)
71 direction of arrow
72 scale
73 handle
74 chip card

The invention claimed is:

1. A treatment device with a magnetic field applicator, the magnetic field applicator comprising a signal generator for generating an electric coil current, and at least one treatment coil for generating a magnetic field when supplied with the coil current, the magnetic field applicator producing a ramped signal curve for the coil current comprised of a plurality of low frequency base pulses of the coil current with ramp-shaped rising amplitudes, which are active during a defined treatment period, which are a component of a plurality of pulse packets composed of the base pulses, the pulse packets having a plurality of envelopes, the envelopes, described by the amplitudes of the base pulses are likewise ramp-shaped, wherein the envelopes of which form the amplitudes of the base pulses of a rising curve segment of the base pulses starting from close to zero, which rises until approximately a midpoint of the treatment period and subsequently forms a constant curve segment corresponding to a maximum current strength, until an end of the treatment period, the treatment device further comprising a device for strength measurement of a patient, wherein a measured value of strength is stored and displayed on a display of the treatment device, the treatment device further comprising a device for at least one of light therapy and oxygen therapy.

2. The treatment device of claim 1, wherein the current amplitudes of the pulse packets follow a rising pulse packet envelope.

3. The treatment device of claim 2, wherein the rising pulse packet envelope comprises a first rising curve segment, which extends over a plurality of treatment and pauses, and continues in a constant further curve segment corresponding to the maximum current strength, which likewise extends over a further plurality of treatment and pauses.

4. The treatment device of claim 1, wherein the current amplitudes of the pulse packets follow a rectangular function.

5. The treatment device of claim 1, wherein the frequencies of the base pulses are at least one frequency of a Fibonacci series, 1, 2, 3, 5, 8, 13, 21, 34, 55, etc. when applied in a region of a patient heart.

6. The treatment device of claim 1, wherein the frequencies of the pulse packets formed by the base pulses, comprises a plurality of treatment periods and pauses, and follow at least one frequency of a Fibonacci series, 1, 2, 3, 5, 8, 13, 21, 34, 55, etc.

7. The treatment device of claim 6, wherein the frequencies of a plurality of larger pulse packets of the plurality of pulse packets, comprises a plurality of treatment periods and pauses and correspond to a least one frequency of a Fibonacci series 1, 2, 3, 5, 8, 13, 21, 34, 55, etc.

8. The treatment device of claim 1, wherein a frequency of a plurality of successive base pulses of the plurality of base pulses and/or the frequencies of a plurality of successive pulse packets of the plurality of pulse packets and/or the frequencies of a plurality of the larger pulse packets formed by the pulse packets can vary over an entire period of use of the magnetic field applicator, and correspond to at least one or more of the frequencies of a Fibonacci series 1, 2, 3, 5, 8, 13, 21, 34, 55, etc.

9. The treatment device of claim 1, characterized in that a frequency of each of a plurality of successive treatment periods separated by a plurality of pauses can vary over an entire period of use of the magnetic field applicator, and correspond to one or more of the frequencies of a Fibonacci series 1, 2, 3, 5, 8, 13, 21, 34, 55, etc.

10. The treatment device of claim 1, wherein the coil current is active in a plurality of active periods of up to 360 microseconds each, and there is a pause between each of the active periods.

11. The treatment device of claim 1, wherein the treatment coil comprises a magnetic core, which is built into the treatment device, and generates a magnetic field emitted from a plane of the treatment device.

12. The treatment device of claim 11, wherein the magnetic field emitted from the plane of the treatment device has a spatial volume and fills a plateau surface in x and y directions of the plane with a homogenous magnetic flux density.

13. The treatment device according to claim 1, wherein a personalized chip card is provided for activating and controlling the treatment device, on which individual data, settings and parameters of a patient are stored for an activation and individualized control of the treatment device.

14. A treatment device with a magnetic field applicator, the magnetic field applicator comprising a signal generator for generating an electric coil current, and at least one treatment coil for generating a magnetic field when supplied with the coil current, the magnetic field applicator producing a ramped signal curve for the coil current comprised of a plurality of low frequency base pulses of the coil current with ramp-shaped rising amplitudes, which are active during a defined treatment period, which are a component of a plurality of pulse packets composed of the base pulses, the pulse packets having a plurality of envelopes, the envelopes, described by the amplitudes of the base pulses are likewise ramp-shaped, wherein the envelopes of which form the amplitudes of the base pulses of a rising curve segment of the base pulses starting from close to zero, which rises until approximately a midpoint of the treatment period and subsequently forms a constant curve segment corresponding to a maximum current strength, until an end of the treatment period, the treatment device further comprising a device for strength measurement of a patient, wherein a measured value of strength is stored and displayed on a display of the treatment device, the treatment device further comprising a device for at least one of light therapy and oxygen therapy, wherein the at least one magnetic field applicator is located in a backrest, a seat or a footrest such that it can be displaced, and wherein a position of the magnetic field applicator is indicated on a scale or displayed on a display of the treatment device.

* * * * *